United States Patent [19]

Morehouse

[11] Patent Number: 5,807,834
[45] Date of Patent: Sep. 15, 1998

[54] COMBINATION OF A CHOLESTEROL ABSORPTION INHIBITOR AND A CHOLESTEROL SYNTHESIS INHIBITOR

[75] Inventor: Lee A. Morehouse, East Lyme, Conn.

[73] Assignee: Pfizer Inc., New York, N.Y.

[21] Appl. No.: 793,802

[22] PCT Filed: Jun. 7, 1995

[86] PCT No.: PCT/IB95/00447

§ 371 Date: Mar. 18, 1997

§ 102(e) Date: Mar. 18, 1997

[87] PCT Pub. No.: WO96/09827

PCT Pub. Date: Apr. 4, 1996

Related U.S. Application Data

[63] Continuation of Ser. No. 308,908, Sep. 20, 1994, abandoned.

[51] Int. Cl.$^6$ .......................... A61K 31/705; A61K 31/56; A61K 31/58; A61K 31/55; A61K 31/35; A61K 31/21

[52] U.S. Cl. .............................. 514/26; 514/171; 514/173; 514/211; 514/451; 514/460; 514/510; 514/824

[58] Field of Search ............................. 514/26, 171, 173, 514/211, 451, 460, 510, 824

[56] References Cited

U.S. PATENT DOCUMENTS

| 4,602,005 | 7/1986 | Malinow | 514/26 |
|---|---|---|---|
| 5,661,145 | 8/1997 | Davis | 514/210 |

FOREIGN PATENT DOCUMENTS

WO 9400480  1/1994  WIPO .

*Primary Examiner*—Kimberly Jordan
*Attorney, Agent, or Firm*—Peter C. Richardson; Gregg C. Benson; A. Dean Olson

[57] ABSTRACT

Pharmaceutical combination compositions including certain cholesterol absorption inhibitors and cholesterol synthesis inhibitors. The compositions are useful for the treatment of hypercholesterolemia and atherosclerosis.

21 Claims, No Drawings

COMBINATION OF A CHOLESTEROL ABSORPTION INHIBITOR AND A CHOLESTEROL SYNTHESIS INHIBITOR

This application was filed under 35 U.S.C. §371 based on PCT/IB95/00447, which was filed on Jun. 7, 1995 which is a continuation of U.S. application Ser. No. 08/308,908 which was filed on Sep. 20, 1994 and is now abandonded.

BACKGROUND OF THE INVENTION

This invention relates to a pharmaceutical combination of cholesterol absorption inhibitors and cholesterol synthesis inhibitors, kits containing such combinations and the use of such combinations to treat hypercholesterolemia and atherosclerosis, in mammals.

Plasma cholesterol levels have been positively correlated with the incidence of clinical events associated with coronary heart disease (CHD). Thus, pharmacological interventions that reduce cholesterol levels in mammals have a beneficial effect on CHD. In particular, decreased plasma low density lipoprotein (LDL) cholesterol levels are associated with decreased atherosclerosis and a decreased risk of CHD, and hypolipidemic agents used in either monotherapy or combination therapy are effective at reducing plasma LDL cholesterol levels and the subsequent risk of CHD.

Cholesterol metabolism in mammals involves a series of pathways including cholesterol absorption in the small intestine, cholesterol biosynthesis in numerous tissues (primarily the liver and small intestine), bile acid biosynthesis in the liver and reabsorption in the small intestine, synthesis of cholesterol-containing plasma lipoproteins by the liver and intestine, catabolism of the cholesterol-containing plasma lipoproteins by the liver and extrahepatic tissues and excretion of cholesterol and bile acids by the liver. These processes are interrelated, thus their regulation is intricate and intended to maintain cellular and plasma cholesterol levels in a fairly narrow range. Accordingly, perturbations in one facet of cholesterol metabolism can have multiple effects.

Such is the case with cholesterol absorption in the small intestine. For example, an increase or a decrease in the percentage of intestinal cholesterol flux that is absorbed ultimately increases or decreases plasma cholesterol concentrations. Examples of agents that inhibit cholesterol absorption include ACAT inhibitors such as Cl-976 (Krause, B. R. et al., Clin. Biochem., 25, 371–377, 1992), 58-035 (Heiden, J. G. et al., J. Up. Res., 24,1127–1134, 1983) and melinamide, stigmastanyl phosphorylcholine and analogs disclosed in EP-430,078A, β-lactam cholesterol absorption inhibitors disclosed in WO 93/02048 and EP 524,595A, sulfated polysaccharides disclosed in U.S. Pat. No. 5,063, 210 and other compounds such as neomycin and naturally occurring plant saponins. In addition, the steroidal glycosides described in WO 93/07167-A1 and U.S. Pat. Nos. 4,602,003 and 4,602,005 have been proposed as useful for the control of hypercholesterolemia. Also, other steroidal glycosides having superior hypocholesterolemic activity are disclosed in commonly assigned PCT application PCT/U.S.93/04092 published as WO 94/00480 (the disclosure of which is hereby incorporated by reference) and commonly assigned PCT applications PCT/IB94/00349 and PCT/IB94/00348 (the disclosures of which are hereby incorporated by reference). The steroidal glycosides specified above inhibit cholesterol absorption thereby decreasing plasma cholesterol levels.

Inhibition of cholesterol biosynthesis has also been demonstrated to be an effective LDL-lowering modality in man. Cholesterol synthesis occurs in multiple tissues, but principally the liver and the intestine. It is a multistep process starting from acetylcoenzyme A catalyzed by a series of enzymes including hydroxymethylglutaryl coenzyme A (HMG-CoA) reductase, HMG-CoA synthase, squalene synthetase, squalene epoxidase, squalene cyclase and lanosterol demethylase. Inhibition of catalysis of these enzymes or blocking HMG-CoA reductase gene expression is recognized as an effective means to reduce cholesterol biosynthesis (thus they are referred to as cholesterol synthesis inhibitors) and can lead to a reduction in cholesterol levels. For example, there are known HMG-CoA reductase inhibitors (e.g., lovastatin, simvastatin, pravastatin, fluvastatin) that are used for the treatment of hypercholesterolemia.

Recently adopted National Cholesterol Education Program guidelines recommend aggressive lipid-lowering therapy for patients with pre-existing cardiovascular disease or those with multiple factors that place them at increased risk. Current monotherapy is usually not sufficient to lower LDL cholesterol to recommended levels, so combination therapy has become more prevalent. GB 2,227,662A discloses combination of an HMG-CoA reductase inhibitor with a bile acid sequestrant. WO 93/17557 A discloses the combination of a squalene synthetase inhibitor with an HMG-CoA reductase inhibitor or other hypolipidemic agents. WO 88/05296 discloses the combination of a HMG-CoA reductase inhibitor with gemfibrozil. Recently combination therapies of 5-C-hydroxymethyl hexose sterols and bile acid binders or cholesterol synthesis inhibitors have been proposed in PCT application no. PCT/US92/08290 (published as WO 93/07167). Also, combination therapies of cholesterol synthesis inhibitors and β-lactam-derived cholesterol absorption inhibitors have been described in PCT application no. PCT/U.S.93/12291 (published as WO 94/14433) as having a synergistic hypolipidemic effect. Nevertheless, in practice, many combinations of existing hypolipidemic agents are contraindicated, limiting the options of prescribing physicians in patients requiring greater reductions of plasma LDL-cholesterol levels than is achievable with monotherapy.

Thus, although there are a variety of hypercholesterolemia therapies there is a continuing need and a continuing search in this field of art for alternative therapies.

SUMMARY OF THE INVENTION

This invention is directed to a pharmaceutical combination composition including a cholesterol absorption inhibitor and a cholesterol synthesis inhibitor for the treatment of hypercholesterolemia and atherosclerosis. The combination comprises a therapeutically effective amount of a first compound, said first compound being a cholesterol absorption inhibitor selected from GROUP IA and GROUP III wherein GROUP IA comprises a compound of Formula IA'

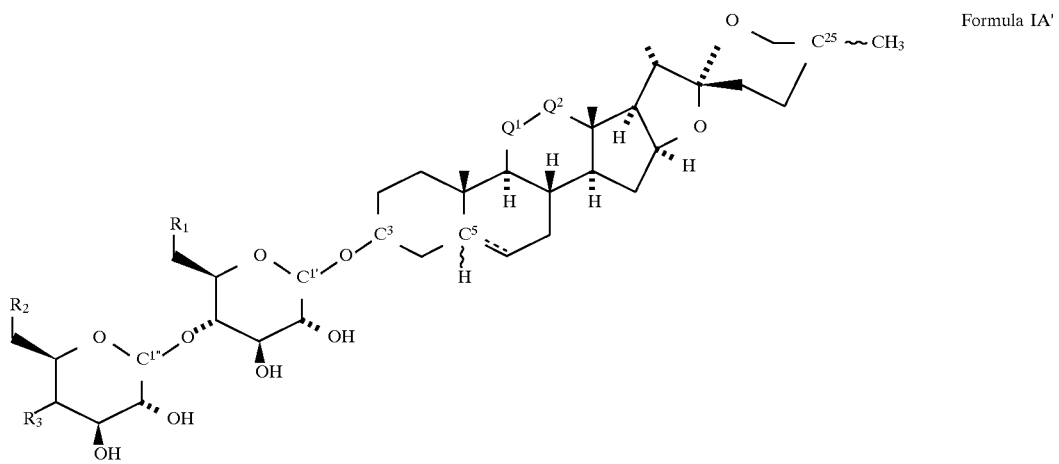

Formula IA' and the pharmaceutically-acceptable salts and hydrates thereof wherein $Q^1$ is methylene, carbonyl,

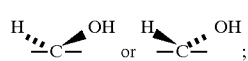

$Q^2$ is methylene, carbonyl,

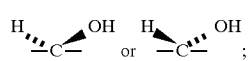

$R_1$, $R_2$, and $R_3$ are independently each hydrogen, hydroxy, halo, amino, azido, $(C_1-C_6)$alkoxy$(C_1-C_6)$alkoxy or —Z—$R_4$;

Z for each occurrence is independently —NH—C(=O)—, —O—C(=O)—, —O—C(=O)—N($R_5$)—, —NH—C(=O)—N($R^5$)— or —O—C(=S)—N($R^5$)—;

$R_4$ for each occurrence is independently aryl, aryl$(C_1-C_6)$alkyl, $(C_2-C_4)$alkenyl, $(C_1-C_6)$alkyl, cyclo$(C_3-C_7)$alkyl or cyclo$(C_3-C_7)$alkyl$(C_1-C_6)$alkyl; each $R_4$ optionally mono-, di-, or tri-substituted independently with halo, $(C_1-C_4)$alkyl, hydroxy, phenoxy, trifluoromethyl, nitro, $(C_1-C_4)$alkoxy, methylenedioxy, oxo, $(C_1-C_4)$alkylsulfanyl, $(C_1-C_4)$alkylsulfinyl, $(C_1-C_4)$alkylsulfonyl, dimethylamino, mono- or di-$(C_1-C_4)$alkylaminocarbonyl, $(C_1-C_4)$alkylcarbonyl, $(C_1-C_4)$alkoxycarbonyl,pyrrolidinylcarbonyl wherein aryl is carbon-linked and is phenyl, furyl, thienyl, pyrrolyl, oxazolyl, isoxazoyl, oxadiazolyl, thiazolyl, isothiazolyl, benzothiazolyl, thiadiazolyl, pyrazolyl, imidazolyl or pyridyl; and $R_5$ for each occurrence is independently hydrogen, $(C_1-C_4)$alkyl or $R_5$ is such that when taken together with the nitrogen to which it is attached and with $R_4$, wherein $R_4$ is a covalent bond, it forms pyrrolidinyl, piperidinyl, N-methylpiperazinyl, indolinyl or morpholinyl and such cyclic group may be substituted on carbon with $(C_1-C_4)$alkoxycarbonyl; with the proviso that $R_1$, $R_2$ and $R_3$ are not all hydroxy; and

GROUP III comprises a compound of Formula IB

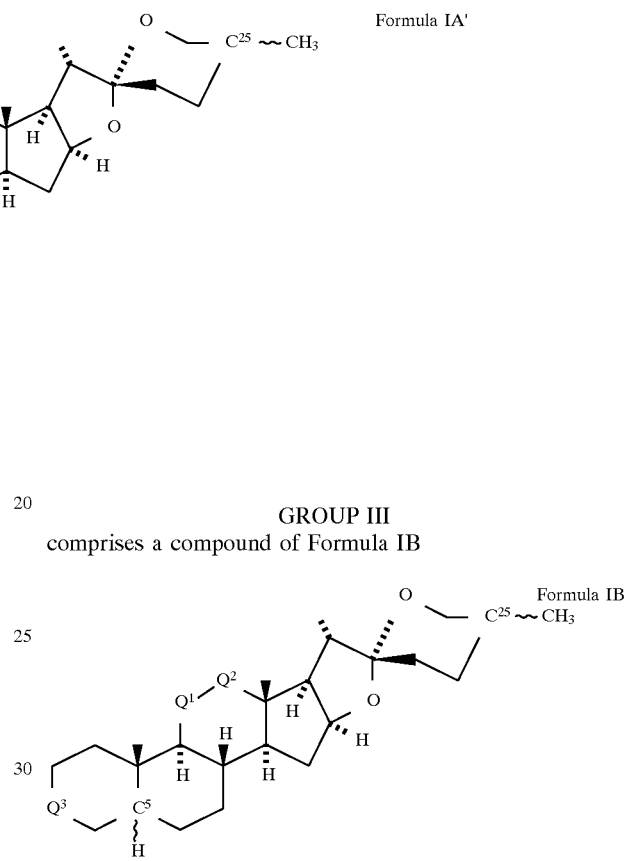

Formula IB wherein $Q^1$ is carbonyl, methylene,

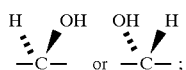

$Q^2$ is carbonyl, methylene,

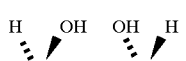

$Q^3$ is

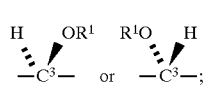

and wherein $R^1$ is
β-D-glucopyranosyl,
β-D-glucopyranuronosyl,
β-D-2-acetamido-2-deoxy-glucopyranosyl,
β-D-galactopyranosyl,
β-D-fucopyranosyl,
β-L-fucopyranosyl,
β-D-xylopyranosyl,
β-L-xylopyranosyl,
α-D-arabanopyranosyl,
α-L-arabanopyranosyl,
α-D-cellobiosyl, β-D-cellobiosyl,
β-D-lactosyl,
β-D-maltosyl,
β-D-gentiobiosyl,
3-O-β-D-galactopyranosyl-α-D-arabanopyranosyl or
β-D-maltotriosyl; and a therapeutically effective amount of a second compound, said compound an HMG-CoA reductase inhibitor, an HMG-CoA synthase inhibitor, an inhibitor of HMG-CoA reductase gene expression, a squalene synthetase inhibitor, a squalene epoxidase inhibitor, a squalene cyclase inhibitor or a lanosterol demethylase inhibitor.

A first group of preferred pharmaceutical compositions consists of those compositions wherein the Group IA' compound is a cholesterol absorption inhibitor selected from GROUP I and GROUP II wherein $R_1$, $R_2$, and $R_3$ are each independently hydrogen, hydroxy, halo, amino, azido, $(C_1-C_6)$alkoxy$(C_1-C_6)$alkoxy or —Z—$R_4$;

Z is —NH—C(=O)—, —O—C(=O)—, —O—C(=O)—N($R^5$)—, —NH—C(=O)—N($R^5$)—or —O—C(=S)—N($R^5$)—;

$R_4$ is $(C_1-C_6)$alkyl, $(C_2-C_{10})$hydroxyalkyl, aryl $(C_1-C_6)$alkyl, trifluoromethyl$(C_1-C_4)$alkyl, $(C_1-C_4)$ alkyloxycarbonyl$(C_1-C_4)$alkyl or aryl wherein aryl is carbon-linked and is phenyl, furyl, thienyl, pyrrolyl, oxazolyl, isooxazoyl, thiazolyl, isothiazolyl, pyrazolyl, imidazolyl or pyridyl and aryl may be mono- di- or tri-substituted with hydroxy, $(C_1-C_6)$alkyl, $(C_1-C_6)$ alkoxy, halo, nitro or trifluoromethyl; and $R_5$ is hydrogen, $(C_1-C_4)$alkyl or $R_5$ is such that when taken together with the nitrogen to which it is attached and with $R_4$, wherein $R_4$ is a covalent bond, it forms pyrrolidinyl, piperidinyl, piperazinyl or morpholinyl;

with the proviso that $R_1$, $R_2$ and $R_3$ are not all hydroxy; and

GROUP I

GROUP I
comprises a compound of Formula I

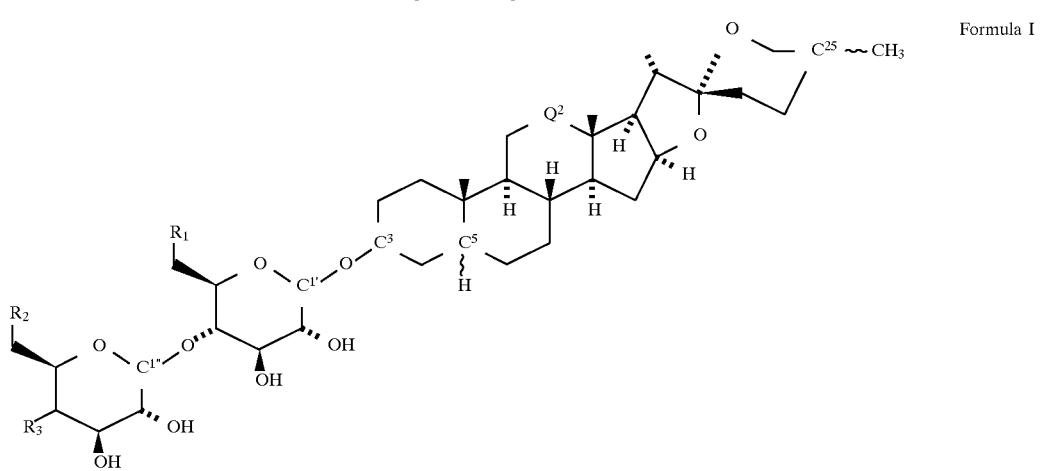

Formula I and the pharmaceutically-acceptable salts and hydrates thereof wherein $Q^2$ is carbonyl, methylene,

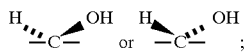

GROUP II

GROUP II
comprises a compound of Formula IA

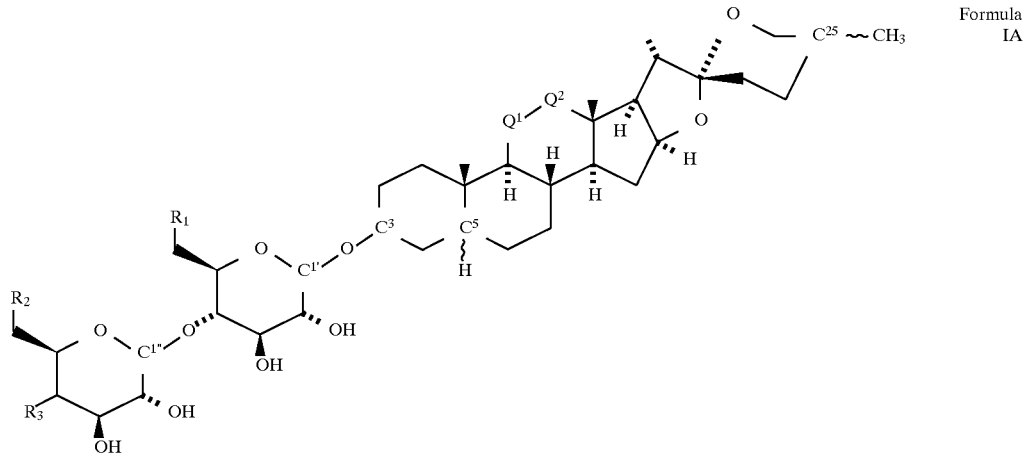

Formula IA and the pharmaceutically-acceptable salts and hydrates thereof wherein $Q^1$ is carbonyl,

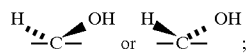

$Q^2$ is methylene, carbonyl,

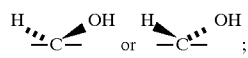

$R_1$, $R_2$, and $R_3$ are each independently hydrogen, hydroxy, halo, amino, azido, $(C_1-C_6)$alkoxy$(C_1-C_6)$alkoxy or —Z—$R_4$;

Z is —NH—C(=O)—, —O—C(=O)—, —O—C(=O)—N($R_5$)—, —NH—C(=O)—N($R^5$)— or —O—C(=S)—N($R^5$)—;

$R_4$ is $(C_1-C_6)$alkyl, $(C_2-C_{10})$hydroxyalkyl, aryl $(C_1-C_6)$ alkyl or aryl wherein aryl is carbon-linked and is phenyl, furyl, thienyl, pyrrolyl or pyridyl and aryl may be mono-, di- or tri- substituted with hydroxy, $(C_1-C_6)$ alkyl, $(C_1-C_6)$alkoxy, halo, nitro or trifluoromethyl; and $R_5$ is hydrogen, $(C_1-C_4)$alkyl or $R_5$ is such that when taken together with the nitrogen to which it is attached and with $R_4$, wherein $R_4$ is a covalent bond, it forms pyrrolidinyl, piperidinyl, piperazinyl or morpholinyl;

with the proviso that $R_1$, $R_2$ and $R_3$ are not all hydroxy.

A second group of preferred pharmaceutical compositions consists of those compositions which additionally include a pharmaceutical carrier.

Within this second group of preferred pharmaceutical compositions is a first group of especially preferred compositions wherein the second compound is an HMG-CoA reductase inhibitor.

Preferred within the immediately preceding group is a group of particularly preferred pharmaceutical compositions wherein the first compound is a compound of Group IA wherein $Q^1$ is methylene.

Preferred within the immediately preceding group are pharmaceutical compositions wherein the first compound is (3β,5α,25R)-3-[(4″,6″-bis-[2-fluorophenylcarbamoyl]-β-D-cellobiosyl)oxy]spirostan-12-one.

Preferred within the immediately preceding group are pharmaceutical compositions wherein the second compound is the HMG-CoA reductase inhibitor lovastatin, simvastatin, pravastatin, flurastatin, atorvastatin or rivastatin.

Within the first group of preferred pharmaceutical compositions is a first group of especially preferred pharmaceutical compositions additionally including a pharmaceutical carrier, and wherein the second compound is an HMG-CoA reductase inhibitor and the first compound is a Formula I compound of Group I GROUP I
comprises a compound of Formula I

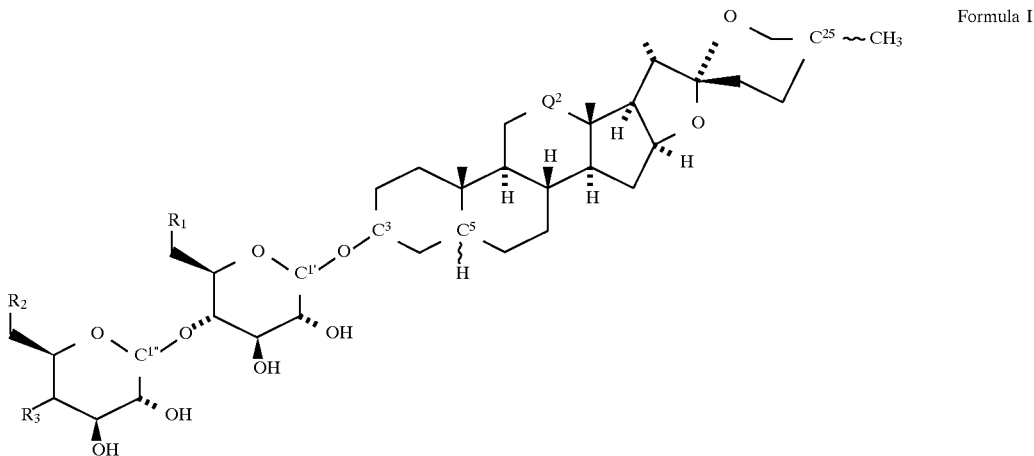

Formula I and the pharmaceutically-acceptable salts and hydrates thereof wherein $Q^2$ is carbonyl, methylene,

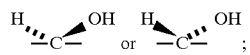 ;

$R_1$, $R_2$, and $R_3$ are each independently hydrogen, hydroxy, halo, amino, azido, $(C_{1-C6})$alkoxy$(C_{1-C6})$alkoxy or —Z—$R_4$;

Z is —NH—C(=O)—, —O—C(=O)—, —O—C(=O)—N($R^5$)—, —NH—C(=O)—N($R^5$)— or —O—C(=S)—N($R^5$)—;

$R_4$ is $(C_1-C_6)$alkyl, $(C_2-C_{10})$hydroxyalkyl, aryl $(C_1-C_6)$alkyl, trifluoromethyl$(C_1-C_4)$alkyl, $(C_1-C_4)$alkyloxycarbonyl$(C_1-C_4)$alkyl or aryl wherein aryl is carbon-linked and is phenyl, furyl, thienyl, pyrrolyl, oxazolyl, isooxazoyl, thiazolyl, isothiazolyl, pyrazolyl, imidazolyl or pyridyl and aryl may be mono- di- or tri-substituted with hydroxy, $(C_1-C_6)$alkyl, $(C_1-C_6)$alkoxy, halo, nitro or trifluoromethyl; and $R_5$ is hydrogen, $(C_1-C_4)$alkyl or $R_5$ is such that when taken together with the nitrogen to which it is attached and with $R_4$, wherein $R_4$ is a covalent bond, it forms pyrrolidinyl, piperidinyl, piperazinyl or morpholinyl; with the proviso that $R_1$, $R_2$ and $R_3$ are not all hydroxy.

Within the first group of especially preferred pharmaceutical compositions is a second group of particularly preferred compositions wherein the first compound is a compound of Group IA wherein $Q^1$ is carbonyl,

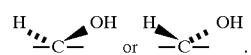 .

Preferred within the immediately preceding group are pharmaceutical compositions wherein the first compound is (3β, 5α, 25R)-3-[(4",6"-bis[thiazol-2-yl-methylcarbamoyl]-β-D-cellobiosyl)oxy]spirostan-11-one or (3β, 5α, 12β, 25R)-3-[(4",6"-bis[2-(methoxycarbonyl)ethylcarbamoyl]-βD-cellobiosy)oxy]-12-hydroxy-spirostan-11-one.

Preferred within the immediately preceding group are pharmaceutical compositions wherein the second compound is lovastatin, simvastatin, pravastatin, fluvastatin, atorvastatin or rivastatin.

Within the first group of preferred pharmaceutical compositions is a second group of especially preferred pharmaceutical compositions additionally including a pharmaceutical carrier, and wherein the second compound is an HMG-CoA reductase inhibitor and the first compound is a Formula IA compound of Group II

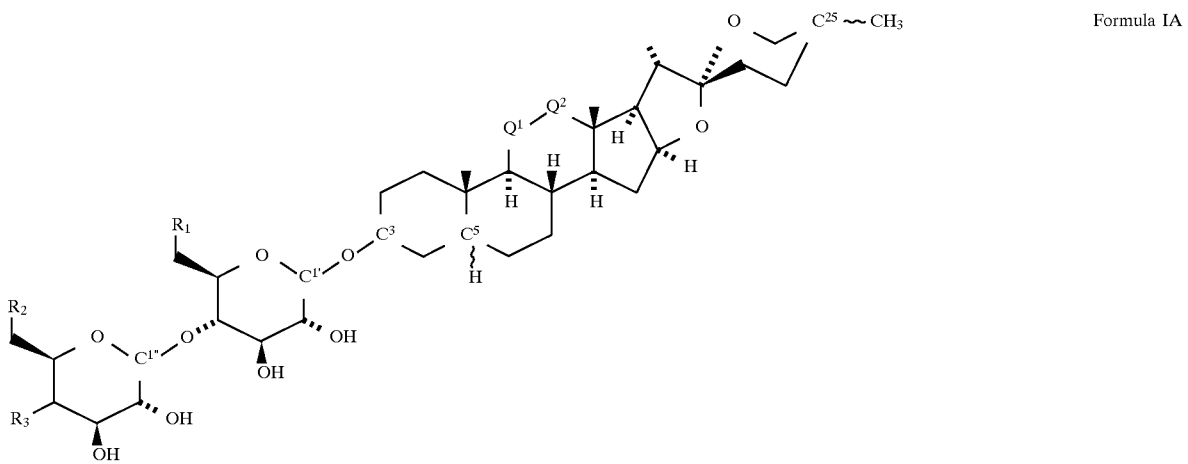

Formula IA and the pharmaceutically-acceptable salts and hydrates thereof wherein $Q^1$ is carbonyl,

or

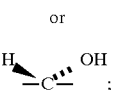 ;

$Q^2$ is methylene, carbonyl, $R_1$, $R_2$, and $R_3$ are each independently hydrogen, hydroxy, halo, amino, azido, $(C_1-C_6)$alkoxy$(C_1-C_6)$alkoxy or —Z—$R_4$;

Z is —NH—C(=O)—, —O—C(=O)—, —O—C(=O)—N($R_5$)—, —NH—C(=O)—N($R^5$)— or —O—C(=S)—N($R^5$)—;

$R_4$ is $(C_1-C_6)$alkyl, $(C_2-C_{10})$hydroxyalkyl, aryl $(C_1-C_6)$ alkyl or aryl wherein aryl is carbon-linked and is phenyl, furyl, thienyl, pyrrolyl or pyridyl and aryl may be mono-, di- or tri- substituted with hydroxy, $(C_1-C_6)$ alkyl, $(C_1-C_6)$alkoxy, halo, nitro or trifluoromethyl; and $R_5$ is hydrogen, $(C_1-C_4)$alkyl or $R_5$ is such that when taken together with the nitrogen to which it is attached and with $R_4$, wherein $R_4$ is a covalent bond, it forms pyrrolidinyl, piperidinyl, piperazinyl or morpholinyl;

with the proviso that $R_1$, $R_2$ and $R_3$ are not all hydroxy.

Within the first group of especially preferred pharmaceutical compositions is a third group of particularly preferred compositions wherein the first compound is a compound of Group III.

Preferred within the immediately preceding group are pharmaceutical compositions wherein the first compound is (3β,5α,25R)-3-((β-D-cellobiosyl)oxy)spirostan-11-one.

Preferred within the immediately preceding group are pharmaceutical compositions wherein the second compound is lovastatin, simvastatin, pravastatin, fluvastatin, atorvastatin or rivastatin.

Within the first group of preferred pharmaceutical compositions is a third group of especially preferred pharmaceutical compositions additionally including a pharmaceutical carrier, and wherein the second compound is an HMG-CoA reductase inhibitor and the first compound is a Formula IB compound of Group III

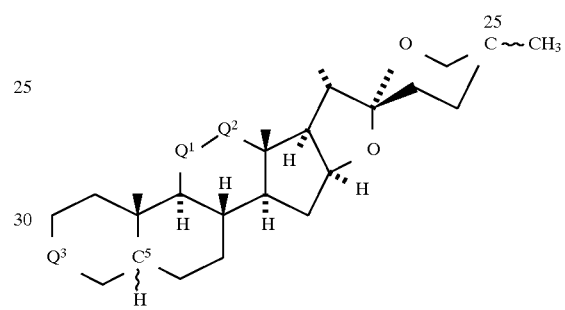

Formula IB wherein $Q^1$ is carbonyl, methylene,

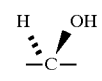

or

 ;

$Q^2$ is carbonyl, methylene,

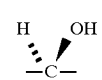

or

 ;

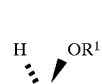

or

 ;

and wherein
$R^1$ is

β-D-glucopyranosyl,
β-D-glucopyranuronosyl,
β-D-2-acetamido-2-deoxy-glucopyranosyl,
β-D-galactopyranosyl,
β-D-fucopyranosyl,
β-L-fucopyranosyl,
β-D-xylopyranosyl,
β-L-xylopyranosyl,
α-D-arabanopyranosyl,
α-L-arabanopyranosyl,
α-D-cellobiosyl,
β-D-cellobiosyl,
β-D-lactosyl,
β-D-maltosyl,
β-D-gentiobiosyl,
3-O-β-D-galactopyranosyl-α-D-arabanopyranosyl or
α-D-maltotriosyl.

Within the second group of preferred pharmaceutical compositions is a second group of especially preferred pharmaceutical compositions wherein the second compound is a squalene synthetase inhibitor selected from a compound of Formula ZQ

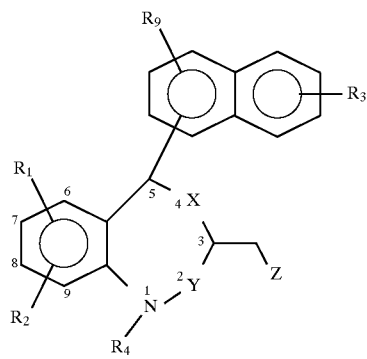

FORMULA ZQ and the pharmaceutically acceptable cationic and anionic salts, prodrugs and stereoisomers thereof
wherein X is oxy, thio, —S(O)— or —S(O)$_2$—;
Y is carbonyl or methylene;
$R_1$, $R_2$, $R_3$ and $R_9$ are each independently hydrogen, halo, hydroxyl, trifluoromethyl, ($C_1$–$C_4$)alkyl, fluorinated ($C_1$–$C_4$)alkyl having from 1 to 9 fluorines, ($C_1$–$C_4$) alkoxy, fluorinated ($C_1$–$C_4$)alkoxy having from 1 to 9 fluorines, ($C_1$–$C_4$)alkylthio, ($C_1$–$C_4$)alkylsulfinyl, ($C_1$–$C_4$)alkylsulfonyl, phenyl, amino, mono-N- or di-N,N-($C_1$–$C_4$)alkylamino, carboxyl, ($C_1$–$C_4$) alkoxycarbonyl, carbamoyl, mono-N- or di-N,N-($C_1$–$C_4$)alkylcarbamoyl, ($C_1$–$C_4$)alkanoylamino, fluorinated ($C_1$–$C_4$)alkanoylamino having from 1 to 9 fluorines, ($C_1$–$C_4$)alkylsulfonylamino or fluorinated ($C_1$–$C_4$)alkylsulfonylamino having from 1 to 9 fluorines, ($C_1$–$C_6$)alkanoyl, ($C_1$–$C_6$)alkanoyl($C_1$–$C_6$) alkyl, oxazolyl, thiazolyl, isoxazolyl, pyrazolyl or isothiazolyl wherein said preceding heterocycles are carbon linked and wherein $R_1$ and $R_2$ can be taken together to form a five, six or seven membered carbocyclic ring or can be taken together to form methylenedioxyl, ethylenedioxyl or propylenedioxyl and such rings formed by taking $R_1$ and $R_2$ together are fused at the 7 and 8 positions;
$R_4$ is ($C_1$–$C_7$)alkyl or ($C_3$–$C_4$)cycloalkylmethyl;
Z is carboxyl, ($C_1$–$C_4$)alkoxycarbonyl, aminocarbonyl, cyano, hydroxyaminocarbonyl, —C(O)N(H)SO$_2$R$_5$, tetrazol-5-yl, 4,5-dihydro-5-oxo-1,2,4oxadiazol-3yl, tetrazol-5-yl-aminocarbonyl, 3-oxoisoxazolidin-4-yl-aminocarbonyl,

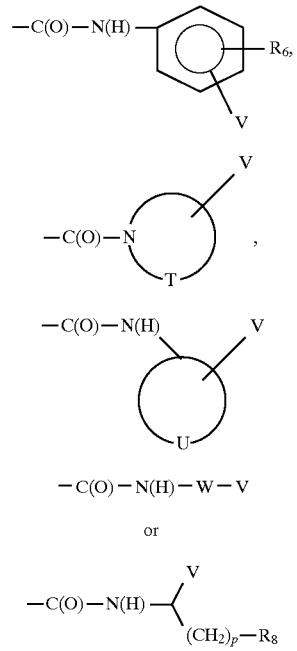

$R_5$ is amino or mono-N- or di-N,N-($C_1$–$C_4$)alkylamino; ($C_1$–$C_4$)alkyl optionally substituted with 1 to 9 fluorines, amino, mono-N- or di-N,N-($C_1$–$C_4$) alkylamino, carboxyl, ($C_1$–$C_4$)alkoxycarbonyl, carbamoyl or mono-N- or di-N,N-($C_1$–$C_4$) alkylcarbamoyl; phenyl optionally mono- or di-substituted independently with methyl, methoxyl, fluoro, trifluoromethoxyl, carboxyl, ($C_1$–$C_4$) alkoxycarbonyl, methylthio, methylsulfinyl, methylsulfonyl, ($C_1$–$C_4$)alkylsulfonylamino or mono-N- or di-N,N-($C_1$–$C_4$)alkylaminosulfonyl; or thiazolyl, isothiazolyl, thienyl, furyl, pyridinyl or such heterocycles optionally mono-substituted by carboxyl, or mono- or di-substituted with methyl;

$R_6$ is hydrogen, hydroxyl or methoxyl;

T forms a five to seven membered mono-aza, saturated ring, said ring optionally containing thio and said ring optionally mono-substituted on carbon with hydroxyl;

U forms a three to seven membered saturated carbocyclic ring;

V is —CO$_2$R$_7$, aminocarbonyl, cyano, tetrazol-5-yl, 4,5-dihydro-5-oxo-1,2,4-oxadiazol-3-yl, tetrazol-5-yl-aminocarbonyl or 3-oxoisoxazolidin4-yl-aminocarbonyl;

$R_7$ is hydrogen or ($C_1$–$C_4$)alkyl;

p is 1, 2, 3 or 4;

$R_8$ is hydroxyl, thiol, carboxyl, ($C_1$–$C_4$)alkoxycarbonyl, carbamoyl, amino, sulfamoyl, ($C_1$–$C_4$)alkoxy, fluorinated ($C_1$–$C_4$)alkoxy having from 1 to 9 fluorines, ($C_1$–$C_4$)alkylthio, ($C_1$–$C_4$)alkylsulfonyl, ($C_1$–$C_4$) alkylsulfinyl, mono-N- or di-N,N-($C_1$–$C_4$) alkylcarbamoyl, mono-N- or di-N,N-($C_1$–$C_4$) alkylamino, ($C_1$–$C_4$)alkylsulfonylamino, fluorinated ($C_1$–$C_4$)alkylsulfonylamino having from 1 to 9 fluorines, ($C_1$–$C_4$)alkanoylamino, fluorinated ($C_1$–$C_4$) alkanoylamino having from 1 to 9 fluorines, mono-N- or di-N,N-($C_1$–$C_4$)alkylaminosulfonyl, ureido, mono-N- or di-N,N-($C_1$–$C_4$)ureido, imidazolyl or pyridyl; and W is pyridyl, pyrimidyl, 1,3,4-oxadiazolyl, 1,3,4-thiadiazolyl, thiazolyl, 1,3,4-triazolyl or oxazolyl.

Preferred within the immediately preceding group are most favored pharmaceutical compositions wherein the first compound is selected from (3β, 5α, 25R)-3-[(4",6"-bis[thiazol-2-yl-methylcarbamoyl]-β-D-cellobiosyl)oxy]spirostan-11-one, (3β, 5α, 12β, 25R)-3-[(4",6"-bis[2-(methoxycarbonyl) ethylcarbamoyl]-β-D-cellobiosyl)oxy] spirostan-11-one, (3β,5α,25R)-3-((β-D-cellobiosyl)oxy)spirostan-11-one or (3β,5α,25R)-3-[(4",6"-bis-[2-fluorophenylcarbamoyl]-β-D-cellobiosyl)oxy]-spirostan-12-one; and (−)-trans-7-chloro-5-(1-naphthyl)-1 -neopentyl-2-oxo-1,2,3,5-tetrahydro-4,1-benzothiazepin-3-acetic acid;

the squalene synthetase inhibitor is (−)-N-trans-(7-chloro-5-(1-naphthyl)-1-neopentyl-2-oxo-1,2,3,5-tetrahydro-4,1-benzothiazepin-3-acetyl)-isonipecotic acid;

(−)-trans-7-chloro-5-(1-naphthyl)-1-neopentyl-2-oxo-1 2,3,5-tetrahydro-4,1-benzoxazepin-3-acetic acid;

(−)-N-(trans-7-chloro-5-(1-naphthyl)-1-neopentyl-2-oxo-1,2,3,5-tetrahydro-4,1-benzoxazepin-3-acetyl)-isonipecotic acid;

(−)-N-(trans-7-chloro-5-(1-naphthyl)-1-neopentyl-2-oxo-1,2,3,5-tetrahydro-4,1-benzoxazepin-3-acetyl)-L-glutamic-α-methyl ester; or (−)-N-(trans-7-chloro-5-(1-naphthyl)-1-neopentyl-1,2,3,5-tetrahydro-4,1-benzoxazepin-3-acetyl)-isonipecotic acid; and Preferred within the most favored group are those pharmaceutical compositions wherein the second compound is (−)-trans-7-chloro-5-(1-naphthyl)-1-neopentyl-2-oxo-1,2,3,5-tetrahydro-4,1-benzoxazepin-3-acetic acid.

Preferred within the most favored group are those pharmaceutical compositions wherein the second compound is (−)-trans-N-(7-chloro-5-(1-napthyl)-1-neopentyl-2-oxo-1,2,3,5-tetrahydro-4,1-benzothiazepin-3-acetyl)-isonipecotic acid.

Preferred within the most favored group are those pharmaceutical compositions wherein the second compound is (−)-N-(trans-7-chloro-5-(1-naphthyl)-1-neopentyl-2-oxo-1,2,3,5-tetrahydro-4,1-benzoxazepin-3-acetyl)-isonipecotic acid.

Preferred within the most favored group are those pharmaceutical compositions wherein the second compound is (−)-N-(trans-7-chloro-5-(1-naphthyl)-1-neopentyl-2-oxo-1,2,3,5-tetrahydro-4,1-benzoxazepin-3-acetyl)-L-glutamic-α-methyl ester.

Preferred within the most favored group are those pharmaceutical compositions wherein the second compound is (−)-N-(trans-7-chloro-5-(1-naphthyl)-1-neopentyl-1,2,3,5-tetrahydro4,1-benzoxazepin-3-acetyl)-isonipecotic acid.

Preferred within the most favored group are those pharmaceutical compositions wherein the second compound is (−)-trans-7-chloro-5-(1-naphthyl)-1-neopentyl-2-oxo-1,2,3,5-tetrahydro4,1-benzothiazepin-3-acetic acid.

Preferred within the above most favored group of pharmaceutical compositions are those compositions wherein the first compound is (3β,5α,25R)-3-((β-D-cellobiosyl)oxy) spirostan-11-one and the second compound is (−)-trans-7-chloro-5-(1-naphthyl)-1-neopentyl-2-oxo-1,2,3,5-tetrahydro-4,1-benzothiazepin-3-acetic acid.

Preferred within the above most favored group of pharmaceutical compositions are those compositions wherein the first compound is (3β,5α,25R)-3-((β-D-cellobiosyl)oxy) spirostan-11-one and the second compound is (−)-trans-N-(7-chloro-5-(1-naphthyl)-1-neopentyl-2-oxo-1,2,3,5-tetrahydro4,1-benzothiazepin-3-acetyl)-isonipecotic acid.

Preferred within the above most favored group of pharmaceutical compositions are those compositions wherein the first compound is (3β,5α,25R)-3-((β-D-cellobiosyl)oxy) spirostan-11-one and the second compound is (−)-trans-7-chloro-5-(1-naphthyl)-1-neopentyl-2-oxo-1,2,3,5-tetrahydro-4,1-benzoxazepin-3-acetic acid.

Preferred within the above most favored group of pharmaceutical compositions are those compositions wherein the first compound is (3β,5α,25R)-3-((β-D-cellobiosyl)oxy) spirostan-11 -one and the second compound is (−)-N-(trans-7-chloro-5-(1-naphthyl)-1-neopentyl-2-oxo-1,2,3,5-tetrahydro4,1-benzoxazepin-3-acetyl)-isonipecotic acid.

Preferred within the above most favored group of pharmaceutical compositions are those compositions wherein the first compound is (3β,5α,25R)-3-((β-D-cellobiosyl)oxy) spirostan-11-one and the second compound is (−)-N-(trans-7-chloro-5-(1-naphthyl)-1-neopentyl-2-oxo-1,2,3,5-tetrahydro4,1-benzoxazepin-3-acetyl)-L-glutamic-α-methyl ester.

Preferred within the above most favored group of pharmaceutical compositions are those compositions wherein the first compound is (3β,5α,25R)-3-((β-D-cellobiosyl)oxy) spirostan-11 -one and the second compound is (−)-N-(trans-7-chloro-5-(1-naphthyl)-1-neopentyl-1,2,3,5-tetrahydro-4, 1-benzoxazepin-3-acetyl)-isonipecotic acid.

Another aspect of this invention is a method for treating hypercholesterolemia in a mammal comprising administering to a mammal suffering from hypercholesterolemia a cholesterol synthesis inhibitor as described above and a cholesterol absorption inhibitor as described above.

Another aspect of this invention is a method for treating atherosclerosis in a mammal comprising administering to a mammal suffering from atherosclerosis a cholesterol synthesis inhibitor as described above and a cholesterol absorption inhibitor as described above.

Yet another aspect of this invention is a kit containing a cholesterol absorption inhibitor described above and a cholesterol synthesis inhibitor described above in separate dosage forms.

In yet another aspect of this invention any of the first compounds of this invention described above (or any compounds selected from any of the above groups of first compounds) and any of the second compounds of this invention described above (or any compound selected from any of the above groups of second compounds) may be used in a synergistic pharmaceutical composition or method of treatment for the above diseases wherein the amount of the first compound alone and the amount of the second compound alone is insufficient to achieve the therapeutic effect and wherein the combined effect of the amounts of the therapeutic agents is greater than the sum of the therapeutic effects achievable with the amounts of the individual therapeutic agents, and a pharmaceutically acceptable diluent or carner.

The compounds of Formulas IA', I, IA and IB are herein defined as the single enantiomer having the absolute stereochemistry depicted in Formulas IA', I, IA and IB respectively.

This invention describes steroidal glycosides in which the sugars are substituted (e.g., with carbamoyl, thiocarbamoyl acyl and silyl groups). In the nomenclature (see Examples and Preparations) all such groups are herein defined as substituted on oxygen unless otherwise designated as deoxy.

The Z moities described above in the steroidal glycosides are herein defined such that they are to be read from left to right (i.e., the left or first atom is attached to the sugar molecule and not to $R_4$).

The $C^5$–$C^6$ dotted line in the above steroidal moiety is herein defined as an optional carbon-carbon double bond.

The parenthetical negative or positive sign used herein in the nomenclature denotes the direction plane polarized light is rotated by the particular stereoisomer.

The chemist of ordinary skill will recognize that certain combinations of heteroatom-containing substituents listed in this invention define compounds which will be less stable under physiological conditions (e.g., those containing acetal or aminal linkages). Accordingly, such compounds are less preferred.

The pharmaceutical combination compositions of this invention result in greater reductions of LDL-cholesterol than is achievable with the same doses of cholesterol absorption inhibitors or cholesterol synthesis inhibitors alone. Thus, these combinations have a synergistic action, decreasing plasma LDL-cholesterol levels to a greater extent than is achievable through use of either agent alone. This invention makes a significant contribution to the art by providing compositions that provide large decreases in plasma cholesterol concentrations resulting in prevention, retardation, and/or regression of atherosclerosis and a decreased risk of CHD.

Other features and advantages will be apparent from the specification and claims which describe the invention.

DETAILED DESCRIPTION OF THE INVENTION

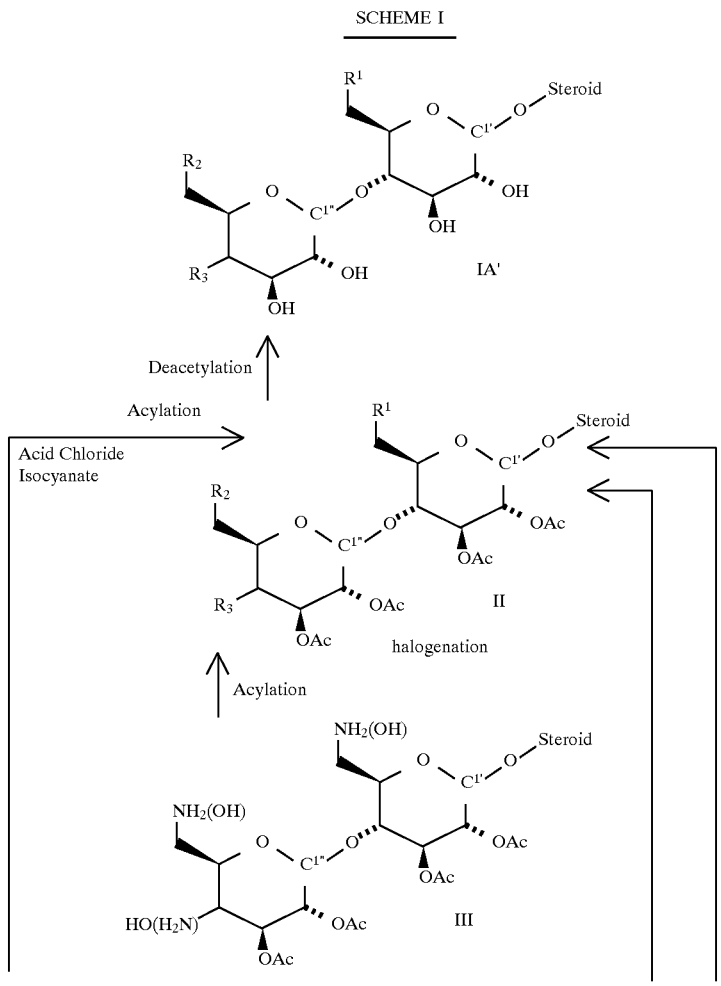

-continued
SCHEME I
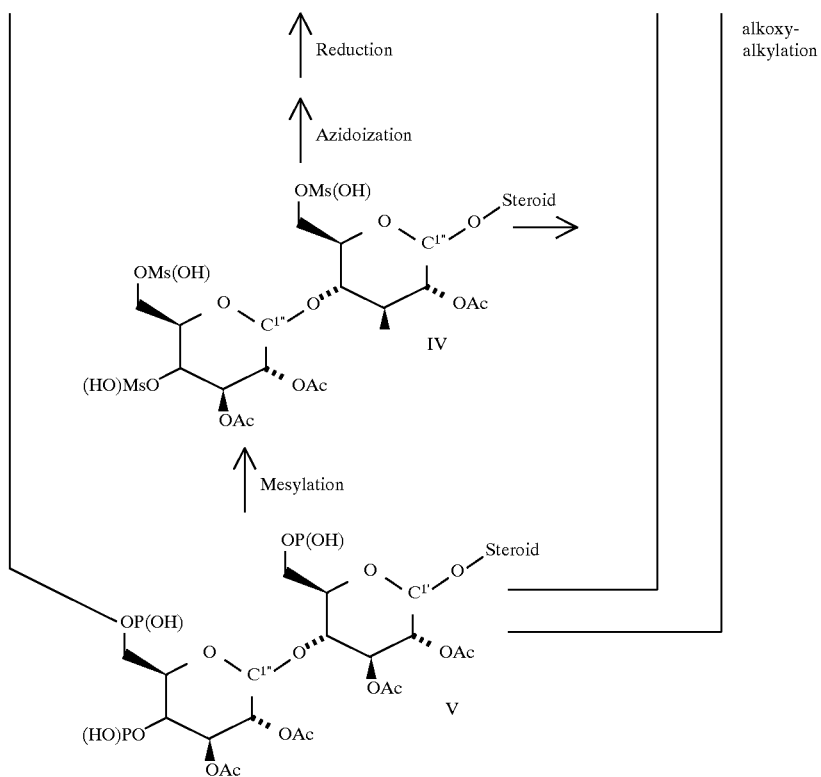

SCHEME III

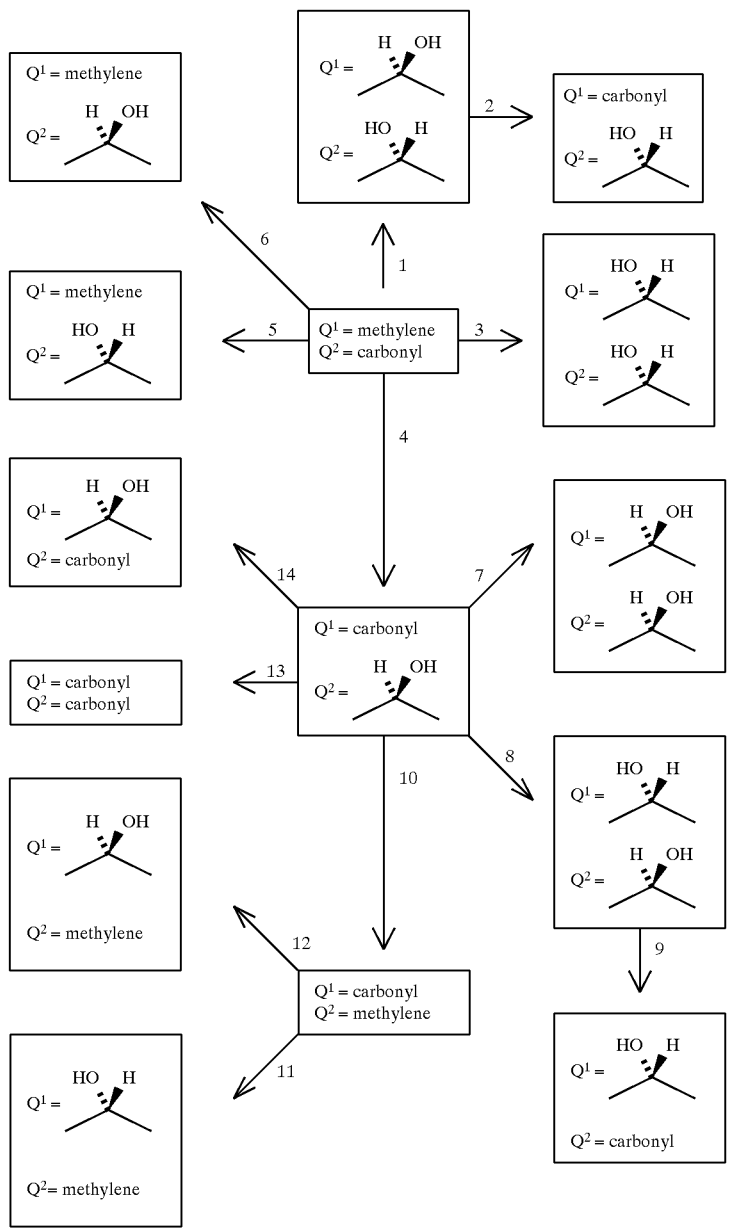

The first compound of this invention is a mammalian cholesterol absorption inhibitor. Exemplary cholesterol absorption inhibitors are described in the Summary of the Invention above. Other cholesterol absorption inhibitors can be identified by their ability to inhibit cholesterol absorption in experimental animals such as the hamster (Harwood et al., J. Lip. Res. 1993; 34:377–95) and will be readily apparent to those skilled in the art.

The cholesterol absorption inhibitor compounds of Formula IA' (described above) may be prepared according to the following methods. Following these methods, procedures for preparing the perhydroxy steroidal glycosidal intermediates and thus the procedures for preparing the compounds of Formula IB (described above) are described.

In general the Formula IA' compounds of this invention may be made by coupling the desired protected sugar halide and steroid followed by deprotection. The desired functionality/substituents are attached (following optional selective protection) and a final deprotection is performed. The following text (which is keyed to the above Schemes) provides a more detailed description.

According to reaction Scheme I, the desired Formula I and IA compounds wherein Steroid is the steroidal moiety of the Formula I and IA compounds described above (i.e., wherein $Q^1$, $Q^2$, $C^3$, $C^5$, $C^{25}$ are as defined above) and $C^{1'}$, $C^{1''}$, $R_1$, $R_2$ and $R_3$ are as defined above may be prepared by deprotecting (e.g., deacetylating) the appropriate Formula II compound wherein Steroid is the steroidal moiety described above, (although hereinafter in the Detailed Description those skilled in the art will realize that in those instances wherein $Q^1$ and/or $Q^2$ is hydroxy the hydroxy may exist in a conventionally protected form as a result of protection of the sugar) $C^{1'}$ and $C^{1''}$ are as defined above and $R_1$, $R_2$, and $R_3$ are as defined above or are a conventionally protected hydroxyl group (—OAc).

Typically the deprotection (preferably the deacetylation), is accomplished by combining the Formula II compound with a nucleophilic base such as sodium methoxide or potassium cyanide in a polar solvent such as methanol, tetrahydrofuran, n-propanol or mixtures thereof at temperatures of about 0° C. to about 100° C. (typically at ambient temperatures) and pressures of about 0.5 psi to about 50 psi (typically ambient) for about 0.25 hour to about 2 hours.

Additionally, the compounds may contain a silyl protecting group which can be removed by treating the deacylated product from above with a quaternary ammonium fluoride such as tetrabutyl ammonium fluoride in an anhydrous solvent such as tetrahydrofuran at temperatures of about 0° C. to about 50° C. (typically at ambient temperatures) for about 0.1 to about 3 hours.

The desired Formula II compounds wherein Steroid is the steroid moiety described above and $C^{1'}$ and $C^{1''}$ are as defined above and at least one of $R_1$, $R_2$ and $R_3$ is hydrogen can be prepared by reduction of the corresponding halogenated compound. Typically, the reduction can be performed by treating the halogenated compound (Br and I preferred) with a reducing agent such as tri-n-butyl tin hydride and a radical initiator such as azoisobutyinitrile (AIBN) in an anhydrous aprotic solvent such as toluene at reflux temperature for about 1 hour to about 5 hours.

The desired Formula II compounds wherein Steroid is the steroidal moiety described above, $C^{1'}$ and $C^{1''}$ are as described above and at least one of $R_1$, $R_2$ and $R_3$ are halogen (or hydroxy) may be prepared by halogenation from the appropriately protected Formula V compound wherein Steroid is the steroidal moiety described above, $C^{1'}$ and $C^{1''}$ are as defined above and $R_1$, $R_2$, and $R_3$ are each independently hydroxy or a conventionally protected hydroxyl group such as —OAc.

Generally the halogenation can be performed by first preparing an appropriately activated and protected form of the Formula V compound (e.g., the Formula IV mesylate) followed by treatment with the desired lithium halide. Typically the mesylation can be performed by combining the Formula V compound and mesyl chloride in the presence of a base, preferably an amine base such as triethylamine and a catalytic amount of a catalyst such as dimethylaminopyridine in an aprotic, anhydrous solvent such as anhydrous dichloromethane at a temperature of about −20° C. to about 20° C. for about one hour to about four hours. The resulting mesylate is then treated with the appropriate lithium halide in a polar solvent such as N,N-dimethylformamide at a temperature of about 70° C. to about 100° C. for about one to about three hours.

Alternatively, the iodination can be performed by combining iodine and the appropriate Formula V compound in an anhydrous aprotic solvent such as toluene (in the presence of imidazole and triphenylphosphine) under reflux conditions and ambient pressure for about four to about eight hours.

Alternatively, the fluorination can be performed by combining the appropriate Formula V compounds with a fluorinating agent such as dialkylaminosulfur trifluoride (e.g., DAST) in an anhydrous, aprotic solvent such as dimethoxyethane or dichloroethane at a temperature of about −10° C. to about 10° C. and then after about twenty minutes to about two hours raising the temperature to about 30° C. to about 60° C. for about one hour to about four hours.

Alternatively, a selective bromination (i.e., $R_2$=Br) can be accomplished by treating the appropriate Formula V compound (wherein $C^{6''}$ and $C^{4''}$ are substituted with OH and $C^{6'}$ is substituted with a conventionally protected hydroxyl group such as —OAc) with carbon tetrabromide and triphenyl phosphine and an amine base such as pyridine in an anhydrous aprotic solvent such as dichloromethane at ambient temperature for about 6 hours to about 48 hours.

The desired Formula II compounds wherein Steroid is the steroidal moiety described above, $C^{1'}$ and $C^{1''}$ are as described above and at least one of $R_1$, $R_2$ and $R_3$ are $(C_1-C_6)$alkoxy$(C_1-C_6)$alkoxy may be prepared by alkylating the appropriately protected Formula V compound wherein Steroid is the steroidal moiety described above, $C^{1'}$ and $C^{1''}$ are as defined above and $R_1$, $R_2$, and $R_3$ are each independently hydroxy (or a conventionally protected hydroxyl group such as —OAc).

Typically, the appropriate Formula V compound is combined with an excess of the appropriate alkoxyalkyl halide and a trialkyl amine base such as diisopropylethylamine in the presence of an anhydrous, aprotic solvent such as dichloroethane at a temperature of about 15° C. to about 35° C. (typically ambient temperature) for about one to about eight hours followed by mixing for one to four hours at a temperature of about 40° C. to about 70° C.

The desired Formula II compounds wherein Steroid is the steroid moiety described above and $C^{1'}$ and $C^{1''}$ are as defined above and at least one of $R_1$, $R_2$, and $R_3$ is Z—$R_4$ and $R_4$ contains a ketone group can be prepared by oxidation of the corresponding hydroxy substituted Formula II compound. Typically the oxidation is performed by treating the hydroxy compound with an oxidizing agent, such as pyridinium chlorochromate, in an anhydrous halogenated solvent such as dichloromethane at 0° C. to about 30° C., generally at ambient temperatures, for about 2 hours to about 24 hours.

Similarly, Formula II compounds described in the above paragraph wherein $R_4$ contains an alkylsulfinyl group may be prepared by oxidation of the corresponding alkylsulfanyl substituted Formula II compound. Typically the appropriate Formula II compound is treated with one equivalent of a peroxy acid such as metachloroperbenzoic acid in an anhydrous halogenated solvent such as dichloromethane at ambient temperature for 1 hour to about 6 hours. The corresponding alkylsulfonyl Formula II compounds can be prepared in an analogous manner using excess peroxy acid.

The desired Formula II compounds wherein Steroid is the steroid moiety described above, and $C^{1'}$ and $C^{1''}$ are as defined above and at least one of $R_1$, $R_2$, and $R_3$ is Z—$R_4$ and $R_4$ is alkylaminocarbonylalkyl can be prepared from the corresponding carboxy alkyl Formula II compounds through an amide forming reaction. Typically the amide is formed by reacting the carboxylic acid with a carboxyl activating agent such as a substituted carbodiimide and hydroxybenzotriazole and a primary or secondary amine chosen to give the desired amide product. The reaction is typically performed in an anhydrous aprotic solvent such as dichloromethane at ambient temperature for about 0.5 hours to about 6 hours. The carboxy alkyl Formula II compounds used in this procedure are typically prepared from the corresponding benzyl ester (the preparation of the benzyl ester being described herein) by a hydrogenolysis reaction. Thus the ester is treated with a hydrogenation catalyst such as palladium on carbon in an alcoholic solvent such as methanol and placed under 1 to 4 atmospheres of hydrogen, typically 2 atmospheres, for about 0.5 to about 8 hours.

The desired Formula I compounds wherein Steroid is the steroidal moiety described above, $C^{1'}$ and $C^{1''}$ are as described above and at least one of $R_1$, $R_2$ and $R_3$ is —O—C(=O)—$R_4$ or —O—C(=O)—N($R^5$)—$R_4$ may be prepared by acylating the appropriate Formula VI compound wherein $Q^1$, $Q^2$, $C^{1'}$ and $C^{1''}$ are as defined above (See Scheme II). Alternatively, the desired formula II compounds wherein at least one of $R_1$, $R_2$ and $R_3$ is —O—C(=O)—$R_4$, —O—C(=O)—N($R^5$)—$R_4$ or —O—C(=S)—N($R^5$)—$R_4$ may be prepared by acylating the appropriately protected Formula V compound wherein Steroid is the steroidal moiety described above, $C^{1'}$ and $C^{1''}$ are as defined above and $C^{6'}$, $C^{6''}$ and $C^{4''}$ are each independently substituted with hydroxy or a conventionally protected hydroxyl group such as —OAc (See Scheme I).

A nonselective mixture of esters and carbamoyloxy substitution at $R_1$ and $R_2$ is achieved by treating the appropriately protected perhydroxy sugar Formula VI compound with the appropriate acid chloride or isocyanate and an amine base that also acts as an anhydrous solvent such as pyridine in the presence of a drying agent such as molecular sieves at a temperature of about –60° C. to about 25° C. for about 5 minutes to about 24 hours while the reaction is allowed to warm to ambient temperature. Different products and product mixes result from the variation of the amount of acid chloride or isocyanate used, the length of reaction time and the reactivity of the acid chloride or isocyanate.

Alternatively, a more selective acylation is performed by treating the appropriately protected (e.g., OAc) steroidal glycoside Formula V compound with the appropriate isocyanate or acid chloride in the presence of a base, preferably an amine base such as triethylamine or pyridine and a catalytic amount of an acylation catalyst such as dimethylaminopyridine in an anhydrous, aprotic solvent such as dichloromethane at a temperature of about –20° C. to about 20° C. The reaction mixture is allowed to warm to ambient temperature for about 10 minutes to about two hours. The carbamoylation can also be achieved by treating the appropriately protected Formula V compound with the appropriate isocyanate in the presence of cuprous chloride in a polar aprotic solvent such as dimethylformamide at ambient temperature for two hours to about 10 hours.

The carbamoylation may also be achieved by treating the appropriately protected Formula V compound with the appropriate isocyanate in the presence of an organotin catalyst such as dibutyl tin dilaurate in an anhydrous aprotic solvent such as dichloromethane at ambient temperature for about 2 hours to about 24 hours.

In addition, the desired Formula II compounds wherein at least one of $R_1$, $R_2$ and $R_3$ are carbamoyloxy or thiocarbamoyloxy moieties may be prepared by treatment of the appropriately protected (e.g., OAc) steroidal glycoside Formula V compound with a phosgene equivalent such as carbonyl diimidazole or a thio-phosgene equivalent such as thiocarbonyl diimidazole in the presence of a base, preferably an amine base such as diisopropylethylamine in an aprotic, anhydrous solvent such as dichloroethane at a temperature of about 15° C. to about 30° C. (typically ambient temperature) for about one to about four hours. The appropriate amine is added and the reaction mixture is stirred at the same temperature for about one hour to about six hours, and heated if necessary to about 40° C. to about 60° C. for about one to about four hours.

The desired Formula II compounds wherein Steroid is the steroidal moiety described above, $C^{1'}$ and $C^{1''}$ are as described above and at least one of $R_1$, $R_2$ and $R_3$ are —NH—C(=O)—$R_4$ or —NH—C(=O)—N($R^5$)—$R_4$ may be prepared by acylating the appropriately protected Formula III compound wherein Steroid is the steroidal moiety described above, $C^{1'}$ and $C^{1''}$ are as defined above and at least one of $R_1$, $R_2$, and $R_3$ are amino or hydroxy.

Typically the amide may be prepared by the treatment of the appropriately protected (e.g., OAc) steroidal glycosidyl amine with the appropriate acid anhydride or acid chloride in an anhydrous, aprotic solvent such as dichloromethane (in the presence of an amine base as appropiate) for about one to about three hours at a temperature of about 0° C. to about 25° C.

Alternatively, the ureas may be prepared by the treatment of the appropriately protected (e.g., OAc) steroidal glycosidyl amine with the appropriate isocyanate in the presence of a base, preferable an amine base such as triethylamine in an anhydrous, aprotic solvent such as dichloromethane for about one to about three hours at a temperature of about 0° C. to about 25° C.

The desired Formula III compound wherein Steroid is the steroidal moiety described above, $C^{1'}$ and $C^{1''}$ are as defined above and at least one of $R_1$, $R_2$, and $R_3$ are amino, azido or hydroxy may be prepared from the corresponding Formula IV mesylated compounds by azide displacement followed if desired by reduction.

Typically the mesylate compound is exposed to a metal azide such as sodium azide in a polar, aprotic solvent such as N,N,-dimethylformamide (in an inert atmosphere) at a temperature of about 70° C. to about 150° C. for about two to about 10 hours. The preparation of such mesylate compounds are described above for the lithium halide halogenation. Typically the azido compounds are reduced to the corresponding amines by exposure to hydrogen gas in the presence of a noble metal catalyst such as palladium on carbon at ambient temperature for about four to about forty eight hours, under pressures of about one to about three atmospheres.

The desired Formula V compound (appropriately protected to yield the desired substitution described above) wherein Steroid is the steroidal moiety described above, $C^{1'}$ and $C^{1''}$ are as defined above and $C^{6'}$, $C^{6''}$ and $C^{4''}$ are each independently substituted with hydroxy or a conventionally protected hydroxyl group such as —OAc may be prepared by conventional protecting group methods of organic synthesis known to those skilled in the art from the corresponding Formula VI compounds wherein $Q^1$, $Q^2$, $C^3$, $C^5$, $C^{25}$, $C^{1'}$ and $C^{1''}$ are as defined above. For a general description of protecting groups and their use, see T. W. Greene, *Protective Groups in Organic Synthesis*, John Wiley & Sons, New York, 1991. In addition, as an aid to the preparation of the above protected steroidal glycosides, the following paragraphs describe the preparation of various protected steroidal glycosides from their hydroxy analogues using a combination of differentially selective protecting groups and sequential protection reactions.

For example, the desired Formula V compound wherein Steroid is the steroidal moiety described above, $C^{1'}$ and $C^{1''}$ are as defined above, $C^{6'}$ and $C^{6''}$ are substituted with hydroxy and $C^{4''}$ is substituted with OP where P is acyl may be conveniently prepared from the corresponding perhydroxy steroidal glycoside by silylation, acylation and desilylation. The appropriate Formula VI compound is reacted with a base, preferably an amine base such as imidazole, a bulky silylating agent selected to afford the desired selective protection such as a trisubstitutedsilylhalide, preferably t-butyldiphenylsilyl chloride and a catalytic amount of a silylation catalyst such as dimethylaminopyridine in an anhydrous, aprotic solvent such as N, N-dimethylformamide at about −20° C. to about 10° C. followed by ambient temperature stirring for about one to about six hours. Upon completion of the silylation, a base, preferably an amine base such as pyridine and an acylating agent selected to afford the desired acyl protecting group defined above such as acetic anhydride are added at ambient temperature and pressure for about three to about twelve hours to achieve acetylation to prepare the desired protected compound. The resulting product is treated with hydrogen fluoride in an anhydrous, aprotic solvent such as pyridine at about −20° C. to about 10° C. followed by ambient temperature stirring for about two to about six hours to prepare the desired selectively protected compound. This product contains hydroxyl groups at the $C^{6'}$ and $C^{6''}$ positions which can be further differentiated by reaction with one equivalent of a protecting group such as acetic anhydride in the presence of a base, such as pyridine at ambient temperatures for about 1 to about 4 hours. This procedure gives a mixture of Formula V compounds which contain a single hydroxyl group at either the $C^{6'}$ or the $C^{6''}$ position which can be separated chromatographically.

In addition, the desired Formula V compound wherein Steroid is the steroidal moiety described above, $C^{1'}$ and $C^{1''}$ are as defined above, $C^{6''}$ and $C^{4''}$ are substituted with hydroxy and $C^{6'}$ is substituted with OP where P is acyl may be conveniently prepared from the corresponding perhydroxy steroidal glycoside by ketalization, acylation and deketalization. The appropriate Formula VI compound is reacted with an acetal or ketal selected to afford the desired cyclic protecting group defined above such as benzaldehyde dimethyl acetal or anisaldehyde dimethyl acetal in the presence of a catalytic amount of a strong acid such as camphorsulfonic acid in an anhydrous, aprotic solvent such as chloroform or dichloroethane under reflux conditions for about two to about six hours at ambient pressure. Upon completion of the ketalization, a base preferably an amine base such as pyridine, a catalytic amount of an acylation catalyst such as dimethylaminopyridine and an acylating agent selected to afford the desired acyl protecting group defined above such as acetic anhydride or chloroacetic anhydride were added at a temperature of about −20° C. to about 10° C. followed by ambient temperature stirring for about one to about twelve hours to prepare the desired protected compound. The resulting product is treated with 80% acetic acid in water at about 50° C. to about reflux conditions for about one to about four hours or with trifluoroacetic acid in a mixture of dichloromethane and methanol at ambient temperature for about two to about eight hours to prepare the desired protected compound.

This product can further be converted to the Formula V compound wherein $C^{6'}$ and $C^{6''}$ are substituted with OP where P is an acyl or silyl protecting group and $C^{4''}$ is substituted with OH by a selective silylation reaction. Typically the silylation is performed by treating the appropriate Formula V compound wherein $C^{4''}$ and $C^{6''}$ are substituted with OH and $C^{6'}$ is substituted with OP where P is an acyl protecting group with a silylating agent such as tert-butyldimethylsilyl chloride and a base preferably an amine base such as imidazole in a polar aprotic solvent such as dimethyl formamide at ambient temperature for about 12 hours to about 48 hours.

The desired Formula V compound wherein Steroid is the steroidal moiety described above, $C^{1'}$ and $C^{1''}$ are as defined above, $C^{6''}$ and $C^{4''}$ are substituted with hydroxy and $C^{6'}$ is substituted with OP where P is an ether protecting group may be conveniently prepared from the corresponding perhydroxy steroidal glycoside by ketalization, etherification and deketalization. The ketalization is performed as described above. Upon completion, the solvent is removed and replaced with a polar aprotic solvent such as dimethylformamide. The appropriate alkyl halide is added such as benzyl bromide, followed by a strong base such as sodium hydride at a temperature of about −20° C. to about 0° C. for about 1 hour to about 12 hours. The deketalization is performed as described above.

The following paragraphs describe the preparations of the Formula VI intermediates for the Formula IA' compounds. They also describe the preparations of the Formula IB compounds.

The desired Formula VI compounds (and also the Formula IB compounds described above) may be prepared from the corresponding Formula VII or Formula VIII peracetylated steroidal glycoside by the deacetylation process described above. For those Formula VI or Formula IB compounds wherein the $C^{1'}$ anomeric oxy is alpha an anomerization is performed on the corresponding Formula VII compound wherein the $C^{1'}$ anomeric oxy is beta prior to deacetylation. The stereochemical terms alpha and beta refer to the configuration of the attachment carbon of the sugar. Typically the anomerization is performed by treatment with a mineral acid such as hydrobromic acid in an anhydrous aprotic solvent such as methylene chloride at temperatures of 20° C. to about 40° C. (typically ambient) for at least 24 hours, typically to several days.

The desired Formula VII compounds may be prepared by coupling the appropriate acetylated sugar halide (e.g., bromide) and steroid. More specifically, for those Formula VII compounds where the sugar is other than beta-D-maltosyl, β-D-gentiobiosyl or β-D-2-acetamido-2-deoxy-glucopyranosyl, a zinc fluoride promoted coupling of the appropriate Formula IX compound and peracetylated sugar halide is used. For those Formula VII compounds where the sugar is beta-D-maltosyl, β-D-gentiobiosyl or β-D-2-acetamido-2-deoxy-glucopyranosyl, a mercuric bromide and mercuric cyanide promoted coupling of the appropriate Formula X compound (e.g., trimethyl silyl ether of the Formula IX compound) and peracetylated sugar halide is used.

Generally, the zinc fluoride promoted coupling of the Formula IX compound and the peracetylated sugar bromide occurs in a non-protic, anhydrous reaction-inert solvent (e.g., acetonitrile) at a temperature of about 20° C. to about 100° C. for about 0.5 to about 12 hours. Typically about 0.5 to about 4 equivalents (based on Formula IX compound) zinc fluoride is used and about 0.5 to about 3 equivalents acetylated sugar bromide is used. Preferably the coupling is acid catalyzed and it is especially preferred that hydrohalic acid generated during the reaction is used as the acid catalyst. The desired compounds may be prepared at pressures of 0.5 to 50 psi, although typically ambient pressures are used. In a preferred isolation technique the glycosides may be precipitated from the crude filtered reaction mixture (e.g., acetonitrile product solution) by the addition of about 25% to 75% water and the remainder alcohol (e.g., methanol). Precipitation of the product from aqueous methanol/acetonitrile requires less processing than an extractive isolation, and provides a product of greater purity. Generally, the mercuric bromide and mercuric cyanide promoted coupling of the Formula X compound and the acetylated sugar bromide is performed in an aprotic, anhydrous solvent such as methylene chloride at a temperature of about 20° C. to about 100° C. for about 0.5 to about 6 hours.

Typically about 0.5 to about 4 equivalents (based on acetylated sugar bromide) mercuric bromide and mercuric cyanide is used and about 0.5 to about 3 equivalents peracetylated sugar bromide is used. The desired compounds may be prepared at pressures of 0.5 to 50 psi, although typically ambient pressures are used. Preferably they are isolated as described for the zinc fluoride promoted coupling of the Formula IX compound.

The desired Formula X compounds are as described above may be prepared by silylating the appropriate Formula IX compound. Generally the Formula IX compound, a base such as triethylamine and an activated trialkylsilyl compound (e.g., trimethylsilyl trifluoromethane sulfonate or trimethylsilyl chloride) are reacted in an aprotic, anhydrous solvent such as methylene chloride at a temperature less than about 10° C. for about 0.5 hour to about two hours.

In general, the procedures described above may be combined thus providing Formula I compounds wherein the $R_1$, $R_2$ and/or $R_3$ groups are dissimilar (e.g., halogenation followed by carbamoylation).

The starting materials for the above described reaction schemes (e.g., alkoxyalkyl halide, acid anhydride, peracetylated sugar halides, acid chlorides, isocyanates, steroids, amines, trialkylsilylchlorides, carbonyl diimidazoles, thiocarbonyl diimidazoles, acid derivatives, acetals, ketals, protecting groups) are readily available or can be easily synthesized by those skilled in the art using conventional methods of organic synthesis. For example some of the compounds of this invention require the synthesis of substituted amines and carboxylic acids which eventually will become $R_4$ groups. Such preparations are standard and known to those skilled in the art.

In addition, as an aid to the preparation of the above steroids, the following paragraphs describe the preparation of the various Formula IX compounds. Literature references for the preparation of Formula IX steroid compounds (wherein $Q^1$ is methylene and $Q^2$ and the stereochemistry of the $C^5$ hydrogen (or lack of the $C^5$ hydrogen) and $C^{25}$ carbon are as defined below) are described in Tables I and II.

TABLE I

Formula IX Compounds Where $Q^1$ is Methylene and the $C^3$ Hydroxy Group is Beta

| $C^5$ hydrogen | $C^{25}$ | $Q^2$ | Reference |
|---|---|---|---|
| α | R | $CH_2$ | R. E. Marker et al., J. Am. Chem. Soc. (1943) 65 1199. |
| α | R | C=O | Marker et al., J. Am. Chem. Soc. (1947) 69, 2167. |
| α | S | $CH_2$ | Goodson & Noller J. Am. Chem. Soc. (1939) 61, 2420. |
| α | S | C=O | Callow & James J. Chem. Soc. (1955) 1671. |
| β | R | $CH_2$ | Marker et al., J. Am. Chem. Soc. (1943) 65, 1199. |
| β | R | C=O | Marker et al., J. Am. Chem. Soc. (1947) 69, 2167. |
| β | S | $CH_2$ | Marker et al., J. Am. Chem. Soc. (1943) 65, 1199. |
| β | S | C=O | Kenney & Wall J. Org. Chem. (1957) 22, 468. |

TABLE II

Formula IX Compounds Where the $C^3$ Hydroxy Group is Beta and There is a Double Bond Between $C^5$—$C^6$

| $C^{25}$ | $Q^2$ | Reference |
|---|---|---|
| R | $CH_2$ | Marker, et al., J. Am. Chem. Soc. (1943) 65 1199 |
| R | C=O | Walens, et al., J. Org. Chem. (1957) 22, 182. |
| S | $CH_2$ | Marker, et al., A. Am. Che. Soc. (1947) 69, 2167. |
| S | C=O | Walens, et al., J. Org. Chem. (1957) 22, 182. |

The following paragraphs describe and/or give literature references for the preparation of the various steroids used as starting materials stereochemistry at the $C^3$ position and the oxygenation and different epimers at $C^{11}$ ($Q^1$) and $C^{12}$ ($Q^2$) from the above Formula IX compounds described in Table I. In general the preparation of the different oxygenated steroids is independent of the stereochemistry at the $C^3$, $C^5$ (or lack of the $C^5$ hydrogen) and $C^{25}$ positions. Thus, once the appropriate stereochemistry at the $C^3$, $C^5$ (or lack of the $C^5$ hydrogen) and $C^{25}$ positions are achieved where $Q^1$ and $Q^2$ are each methylene or where $Q^1$ is methylene and $Q^2$ is carbonyl, the various oxygenated compounds at $Q^1$ and $Q^2$ may be prepared therefrom.

Some of the preparation methods described herein will require protection of remote functionality (i.e., $C^{11}$ ($Q^1$) and $C^{12}(Q^2)$). The need for these protecting groups will vary depending on the nature of the remote functionality and the conditions of the preparation methods. This need is readily determined by one skilled in the art. For a general description of protecting groups and their use, see T. W. Greene, Protective Groups in Organic Synthesis, John Wiley & Sons, New York, 1981.

The Formula IX compounds wherein $Q^1$ is methylene, $Q^2$ is either methylene or carbonyl and the $C^3$ hydroxy is beta may be converted to the corresponding Formula VIII compounds where the $C^3$ hydroxy is alpha by the following two procedures. These preparative methods may be used independent of the $C^{25}$ stereochemistry.

If $Q^2$ is carbonyl, the carbonyl is protected as a ketal (e.g., ethylene ketal), by reacting the steroid with ethylene glycol and an acid catalyst according to the procedure of Engel and Rakhit, Can. J. Chem, 40, 2153, 1962. When the $C^5$ hydrogen is alpha, the $C^3$ hydroxy group is oxidized to the ketone using pyridinium chloro chromate (PCC) in methylene chloride at ambient conditions. Then the $C^3$ ketone is reduced with a sterically hindered reducing agent such as K-Selectride® reducing agent, at low temperature in tetrahydrofuran to give the $C^3$ alpha alcohol according to Gondos and Orr, J. Chem. Soc. Chem. Commun. 21, 1239, 1982. If appropriate, the $Q^2$ protecting group is removed with acid, such as hydrochloric acid, in an appropriate solvent such as acetone.

For those compounds wherein the $C^5$ hydrogen is beta the same procedures are used as were used when the $C^5$ hydrogen is alpha except the $C^3$ ketone is reduced using sodium borohydride in ethanol to furnish the $C^3$ alpha alcohol.

Reaction Scheme III illustrates the reaction pathways to achieve the Formula IX compounds wherein $Q^1$ ($C^{11}$) and $Q^2$ ($C^{12}$) are defined above starting from the Formula IX compound wherein $Q^1$ is methylene and $Q^2$ is carbonyl.

In general, preparation methods for these compounds may be found in L. F. Fieser and M. Fieser, Steroids, Reinhold Pub. Corp., New York, 1959 and references therein, however, the following descriptive text (which is keyed to Reaction Scheme III) provides specific guidance.

Briefly according to Reaction Scheme III method 1, the starting material is acetylated and bromininated according to the procedure described in J. Chem. Soc., 1956, 4344. This intermediate is then reduced with lithium aluminum hydride and treated with silver oxide by a procedure similar to that described in Helv. Act. Chim., 1953, 36, 1241. The resulting β-11,12-epoxide is opened with trichloroacetic acid, saponified and reduced with zinc and acetic acid using the procedure described in J. Chem. Soc., 1956, 4330 to give the product shown for method 1.

In method 2, the starting material is selectively acetylated using the procedure described in J. Chem. Soc., 1956, 430. Using the procedure described in Org. Syn., 1976, 55, 84, the resulting product is oxidized with chromium trioxide and pyridine. Using the procedure described in *Synthesis,* 1973, 790, the resulting product is saponified with potassium cyanide in water, methanol and THF to give the product shown for method 2.

In method 3, the starting material is converted to the corresponding toluenesulfonylhydrazone which is in turn treated with sodium methoxide using a procedure similar to that described in J. Am. Chem. Soc., 1954, 76, 4013. The resulting 11-ene product is oxidized with osmium tetroxide and the N-methylmorpholine-N-oxide according to the procedure describe in Tetrahedron Letters, 1976, 1973 to give the product shown for method 3.

In method 4, the starting material is monobrominated using a procedure described in US Pat. No. 3,178,418. Hydrolysis of this intermediate using the procedure described in J. Chem. Soc., 1956, 4330 gives the product shown for method 4.

In methods 5 and 6, the starting material is reduced with lithium aluminum hydride according to the procedure described in J. Am. Chem. Soc., 1954, 76, 4013. The two products shown in methods 5 and 6 are separated chromatographically.

In method 7, the starting material is reduced with lithium aluminum hydride according to the procedure described in J. Am. Chem. Soc., 1951, 73,1777 to give the product shown.

In method 8, the starting material is reduced with lithium and ammonia according to the procedure described in J. Am. Chem. Soc., 1953, 75,1282 to give the product shown.

In method 9, the starting material is acetylated according to the procedure described in J. Am. Chem. Soc., 1955, 77, 1632 to give a mixture of acetates from which the 3,11 -diacetate can be isolated. The unprotected 12-alcohol is then oxidized with chromium trioxide and pyridine according to the procedure described in Org. Syn., 1976, 55, 84. Saponification of the acetates gives the product shown for method 9.

In method 10, the starting material is diacetylated using the procedure described in J. Chem. Soc., 1956, 4330. The diacetate is reduced with calcium and ammonia using the procedure described in J. Chem. Soc., 1956, 4334 to give the product shown for method 10.

In method 11, the starting material is reduced with lithium and ammonia according to the procedure described in J. Am. Chem. Soc., 1953, 75,1282 to give the product shown.

In method 12, the starting material is reduced with lithium aluminum hydride according to the procedure described in J. Am. Chem. Soc., 1951, 73, 1777 to give the product shown.

In method 13, the starting material is selectively protected at the 3-alcohol with t-butyldimethylchlorosilane and imidazole using the procedure described in J. Am. Chem. Soc., 1972, 94, 6190. Using the procedure described in Org. Syn., 1976, 55, 84, the product is oxidized with chromium trioxide and pyridine. The 3-alcohol is then desilylated with hydrofluoric acid in acetonitrile using the procedure described in J. Am. Chem. Soc., 1972, 94, 6190 to give the product shown for method 13.

In method 14, the starting material is selectively protected at the 3-alcohol with t-butyldimethylchlorosilane and imidazole using the procedure described in J. Am. Chem. Soc., 1972, 94, 6190. The resulting intermediate is reduced with lithium aluminum hydride using the procedure described in J. Am. Chem. Soc., 1951, 73, 1777. The resulting intermediate is selectively acetylated on the 12-alcohol, silylated on the 11-alcohol with trimethylsilyltriflate and 2,6-lutidine using the procedure described in Tetrahedron Letters, 1981, 22, 3455, and then deacetylated at the 12-alcohol with lithium aluminum hydride and an aqueous ammonium chloride quench. The 12-alcohol is oxidized with chromium trioxide and pyridine in methylene chloride using the procedure described in Org. Syn., 1976, 55, 84, and then desilylated with hydrofluoric acid in acetonitrile using the procedure described in J. Am. Chem. Soc., 1972, 94, 6190 to give the product shown in method 14.

The compounds of Formula IA' which have been obtained and have asymmetric carbon atoms can be separated into their diastereomers on the basis of their physical chemical differences by methods known per se., for example, by chromatography and/or fractional crystallization.

The compounds of this invention may contain acidic or basic functional groups which form salts. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, many of the compounds of this invention may be isolated as hydrates.

In addition, a preferred crystalline monohydrate of (3β, 5α, 25R)-3-[(β-D-cellobiosyl)oxy] spirostan-11-one may be prepared by slurrying the compound in methanol at elevated temperatures followed by crystallization.

Finally, a preferred crystalline form of (3β, 5α, 25R)-3-[(β-D-4", 6"-bis-[2-fluorophenyl-carbamoyl]cellobiosyl)oxy]-spirostan-12-one that for example, can exist as a thin flake with a mixture of rod and doubly terminated blades habit may be prepared by slurrying the compound in ethyl acetate or acetonitrile at elevated temperatures followed by crystallization.

The second compound of this invention is a mammalian cholesterol synthesis inhibitor. The following paragraphs describe exemplary cholesterol synthesis inhibitors in greater detail.

Any HMG-CoA reductase inhibitor may be used as the second compound of this invention. The term HMG-CoA reductase inhibitor refers to compounds which inhibit the bioconversion of hydroxymethylglutaryl-coenzyme A to mevalonic acid catalyzed by the enzyme HMG-CoA reductase. Such inhibition is readily determined by those skilled in the art according to standard assays (e.g., Meth. Enzymol. 1981; 71:455–509 and references cited therein). A variety of these compounds are described and referenced below however other HMG-CoA reductase inhibitors will be known to those skilled in the art. U.S. Pat. No. 4,231,938 (the disclosure of which is hereby incorporated by reference) discloses compounds isolated after cultivation of a microorganism belonging to the genus Aspergillus, such as lovastatin. Also, U.S. Pat. No. 4,444,784 (the disclosure of which is hereby incorporated by reference) discloses synthetic derivatives of the aforementioned compounds, such as simvastatin. Also, U.S. Pat. No. 4,739,073 (the disclosure of which is incorporated by reference) discloses substituted indoles, such as fluvastatin. Also, U.S. Pat. No. 4,346,227 (the disclosure of which is incorporated by reference) discloses ML-236B derivatives, such as pravastatin. Also, EP491226A (the disclosure of which is incorporated by reference) discloses certain pyridyldihydroxyheptenoic acids, such as rivastatin. In addition, U.S. Pat. No. 4,647,576 (the disclosure of which is incorporated by reference) discloses 6-[2-(substituted-pyrrol-1-yl)alkyl]pyran-2-ones such as atorvastatin.

Any HMG-CoA synthase inhibitor may be used as the second compound of this invention. The term HMG-CoA synthase inhibitor refers to compounds which inhibit the biosynthesis of hydroxymethylglutaryl-coenzyme A from acetyl-coenzyme A and acetoacetyl-coenzyme A, catalyzed by the enzyme HMG-CoA synthase. Such inhibition is readily determined by those skilled in the art according to standard assays (Meth Enzymol. 1975; 35:155–160: Meth. Enzymol. 1985; 110:19–26 and references cited therein). A variety of these compounds are described and referenced below however other HMG-CoA synthase inhibitors will be known to those skilled in the art. U.S. Pat. No. 5,120,729 (the disclosure of which is hereby incorporated by reference) discloses beta-lactam derivatives. U.S. Pat. No. 5,064,856 (the disclosure of which is hereby incorporated by reference) discloses spiro-lactone derivatives prepared by culturing a microorganism (MF5253). U.S. Pat. No. 4,847,271 (the disclosure of which is hereby incorporated by reference) discloses oxetane compounds such as 11-(3-hydroxymethyl-4-oxo-2-oxetayl)-3,5,7-trimethyl-2,4-undeca-dienoic acid derivatives.

Any compound that decreases HMG-CoA reductase gene expression may be used as the second compound of this invention. These agents may be HMG-CoA reductase transcription inhibitors that block the transcription of DNA or translation inhibitors that prevent translation of mRNA coding for HMG-CoA reductase into protein. Such compounds may either affect transcription or translation directly, or may be biotransformed to compounds that have the aforementioned activities by one or more enzymes in the cholesterol biosynthetic cascade or may lead to the accumulation of an isoprene metabolite that has the aforementioned activities. Such regulation is readily determined by those skilled in the art according to standard assays (Meth. Enzymol. 1985; 110:9–19). Several compounds are described and referenced below however other inhibitors of HMG-CoA reductase gene expression will be known to those skilled in the art. U.S. Pat. No. 5,041,432 (the disclosure of which is incorporated by reference) discloses 15-substituted lanosterol derivatives. Other oxygenated sterols that suppress synthesis of HMG-CoA reductase are discussed by E. I. Mercer (Prog.Up.Res. 1993;32:357–416).

Any squalene synthetase inhibitor may be used as the second compound of this invention. The term squalene synthetase inhibitor refers to compounds which inhibit the condensation of 2 molecules of farnesylpyrophosphate to form squalene, catalyzed by the enzyme squalene synthetase. Such inhibition is readily determined by those skilled in the art according to standard assays (Meth. Enzymol. 1969; 15: 393–454 and Meth. Enzymol. 1985; 110:359–373 and references contained therein). A variety of these compounds are described in and referenced below however other squalene synthetase inhibitors will be known to those skilled in the art. U.S. Pat. No. 5,026,554 (the disclosure of which is incorporated by reference) discloses fermentation products of the microorganism MF5465 (ATCC 74011) including zaragozic acid. A summary of other patented squalene synthetase inhibitors has been compiled (Curr. Op. Ther. Patents (1993) 861–4).

In particular, the squalene synthesis inhibitors described above (in the Summary of the Invention) are useful as the second compound (mammalian cholesterol synthesis inhibitor) of this invention. These compounds are the subject of commonly assigned U.S. application Ser. No. 08/362,713 filed on Dec. 23, 1994 and commonly assigned PCT/IB95/XXXXX application (Assignee's Docket No. PC8884A) which designates the United States. The disclosures of these applications are hereby incorporated by reference. In addition, as an aid to the preparation of these compounds the description of the compounds is herein repeated and the following Reaction Schemes and accompanying text describe the preparation of such compounds. The description of the substituents should not be confused with the description of the substituents for the cholesterol absorption inhibitors described above.

A compound of Formula ZQ

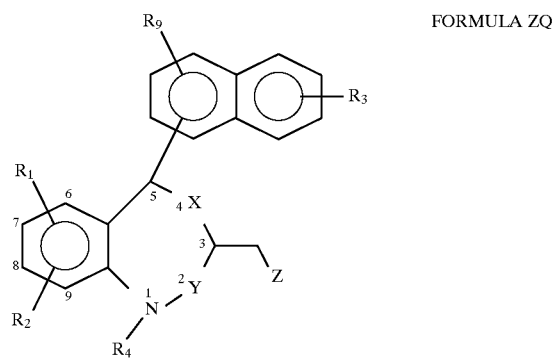

FORMULA ZQ and the pharmaceutically acceptable cationic and anionic salts, prodrugs and stereoisomers thereof wherein X is oxy, thio, —S(O)— or —S(O)$_2$—;

Y is carbonyl or methylene;

$R_1$, $R_2$, $R_3$ and Rg are each independently hydrogen, halo, hydroxyl, trifluoromethyl, ($C_1$–$C_4$)alkyl, fluorinated ($C_1$–$C_4$)alkyl having from 1 to 9 fluorines, ($C_1$–$C_4$) alkoxy, fluorinated ($C_1$–$C_4$)alkoxy having from 1 to 9 fluorines, ($C_1$–$C_4$)alkylthio, ($C_1$–$C_4$)alkylsulfinyl, ($C_1$–$C_4$)alkylsulfonyl, phenyl, amino, mono-N- or di-N,N-($C_1$–$C_4$)alkylamino, carboxyl, ($C_1$–$C_4$) alkoxycarbonyl, carbamoyl, mono-N- or di-N,N-($C_1$–$C_4$)alkylcarbamoyl, ($C_1$–$C_4$)alkanoylamino, fluorinated ($C_1$–$C_4$)alkanoylamino having from 1 to 9 fluorines, ($C_1$–$C_4$)alkylsulfonylamino or fluorinated ($C_1$–$C_4$)alkylsulfonylamino having from 1 to 9 fluorines, ($C_1$–$C_6$)alkanoyl, ($C_1$–$C_6$)alkanoyl($C_1$–$C_6$) alkyl, oxazolyl, thiazolyl, isoxazolyl, pyrazolyl or isothiazolyl wherein said preceding heterocycles are carbon linked and wherein $R_1$ and $R_2$ can be taken together to form a five, six or seven membered carbocyclic ring or can be taken together to form methylenedioxyl, ethylenedioxyl or propylenedioxyl and such rings formed by taking $R_1$ and $R_2$ together are fused at the 7 and 8 positions;

$R_4$ is ($C_1$–$C_7$)alkyl or ($C_3$–$C_4$)cycloalkylmethyl;

Z is carboxyl, ($C_1$–$C_4$)alkoxycarbonyl, aminocarbonyl, cyano, hydroxyaminocarbonyl, —C(O)N(H)SO$_2$R$_5$, tetrazol-5-yl, 4,5-dihydro-5oxo-1,2,4oxadiazol-3yl, tetrazol-5-yl-aminocarbonyl, 3-oxoisoxazolidin-4-yl-aminocarbonyl,

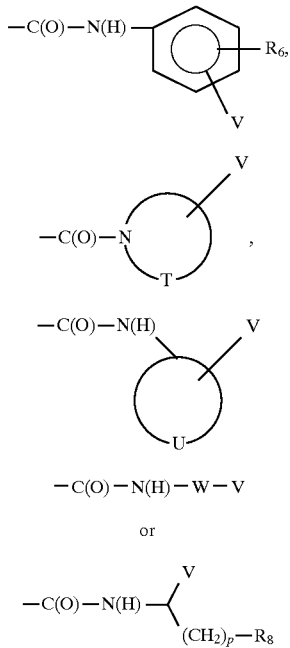

$R_5$ is amino or mono-N- or di-N,N-$(C_1-C_4)$alkylamino; $(C_1-C_4)$alkyl optionally substituted With 1 to 9 fluorines, amino, mono-N- or di-N,N-$(C_1-C_4)$alkylamino, carboxyl, $(C_{1-4})$alkoxycarbonyl, carbamoyl or mono-N- or di-N,N-$(C_1-C_4)$alkylcarbamoyl; phenyl optionally mono- or di-substituted independently with methyl, methoxyl, fluoro, trifluoromethoxyl, carboxyl, $(C_1-C_4)$alkoxycarbonyl, methylthio, methylsulfinyl, methylsulfonyl, $(C_1-C_4)$ alkylsulfonylamino or mono-N- or di-N,N-$(C_1-C_4)$ alkylaminosulfonyl; or thiazolyl, isothiazolyl, thienyl, furyl, pyridinyl or such heterocycles optionally mono-substituted by carboxyl, or mono- or di-substituted with methyl;

$R_6$ is hydrogen, hydroxyl or methoxyl;

T forms a five to seven membered mono-aza, saturated ring, said ring optionally containing thio and said ring optionally mono-substituted on carbon with hydroxyl;

U forms a three to seven membered saturated carbocyclic ring;

V is —$CO_2R_7$, aminocarbonyl, cyano, tetrazol-5-yl, 4,5-dihydro-5-oxo-1,2,4-oxadiazol-3-yl, tetrazol-5-yl-aminocarbonyl or 3-oxoisoxazolidin-4-yl-aminocarbonyl;

$R_7$ is hydrogen or $(C_1-C_4)$alkyl;

p is 1, 2, 3 or 4;

$R_8$ is hydroxyl, thiol, carboxyl, $(C_1-C_4)$alkoxycarbonyl, carbamoyl, amino, sulfamoyl, $(C_1-C_4)$alkoxy, fluorinated $(C_1-C_4)$alkoxy having from 1 to 9 fluorines, $(C_1-C_4)$alkylthio, $(C_1-C_4)$alkylsulfonyl, $(C_1-C_4)$ alkylsulfinyl, mono-N- or di-N,N-$(C_1-C_4)$ alkylcarbamoyl, mono-N- or di-N,N-$(C_1-C_4)$ alkylamino, $(C_1-C_4)$alkylsulfonylamino, fluorinated $(C_1-C_4)$alkylsulfonylamino having from 1 to 9fluorines, $(C_1-C_4)$alkanoylamino, fluorinated $(C_1-C_4)$ alkanoylamino having from 1 to 9 fluorines, mono-N- or di-N,N-$(C_1-C_4)$alkylaminosulfonyl, ureido, mono-N- or di-N,N-$(C_1-C_4)$ureido, imidazolyl or pyridyl; and W is pyridyl, pyrimidyl, 1,3,4-oxadiazolyl, 1,3,4-thiadiazolyl, thiazolyl, 1,3,4-triazolyl or oxazolyl.

REACTION SCHEME I

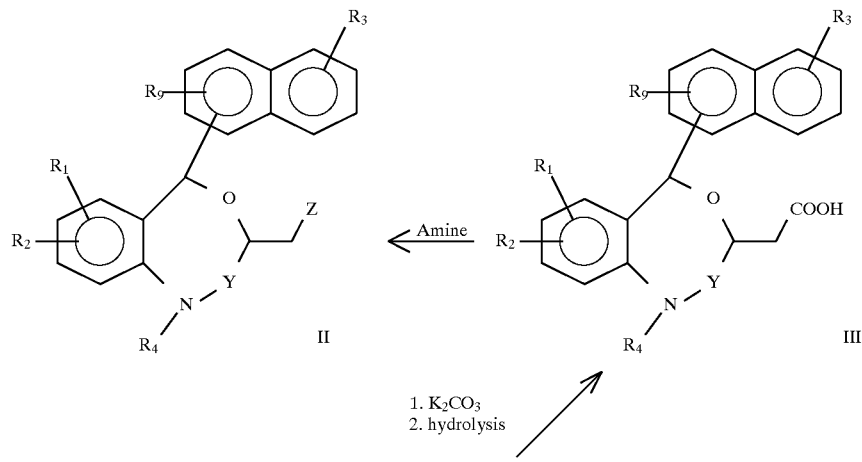

-continued
REACTION SCHEME I
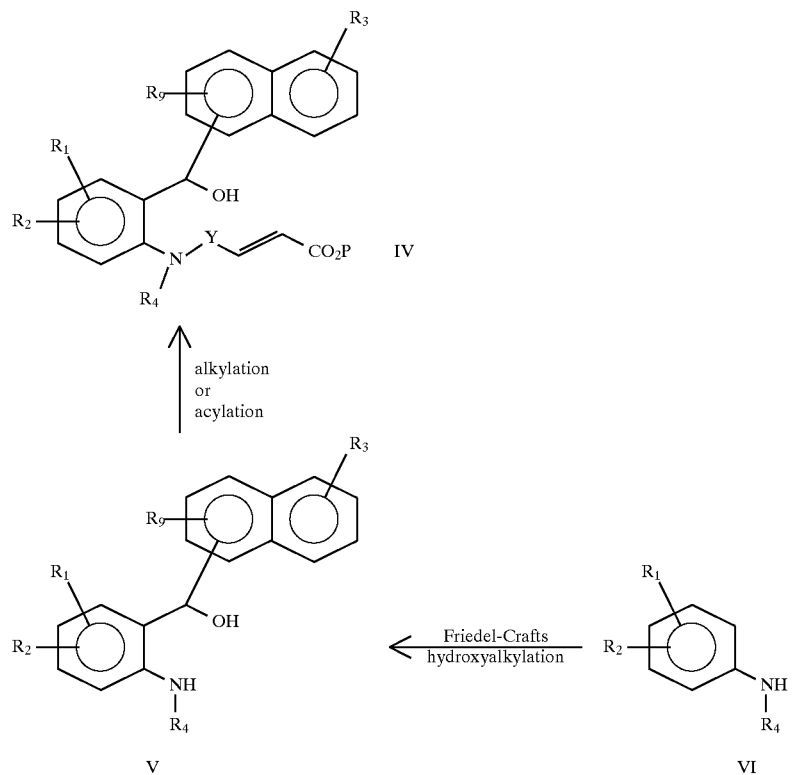
REACTION SCHEME II
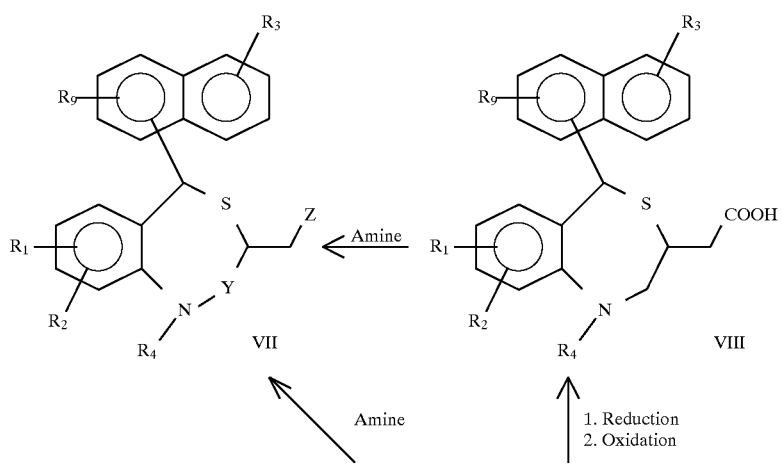

-continued
REACTION SCHEME II

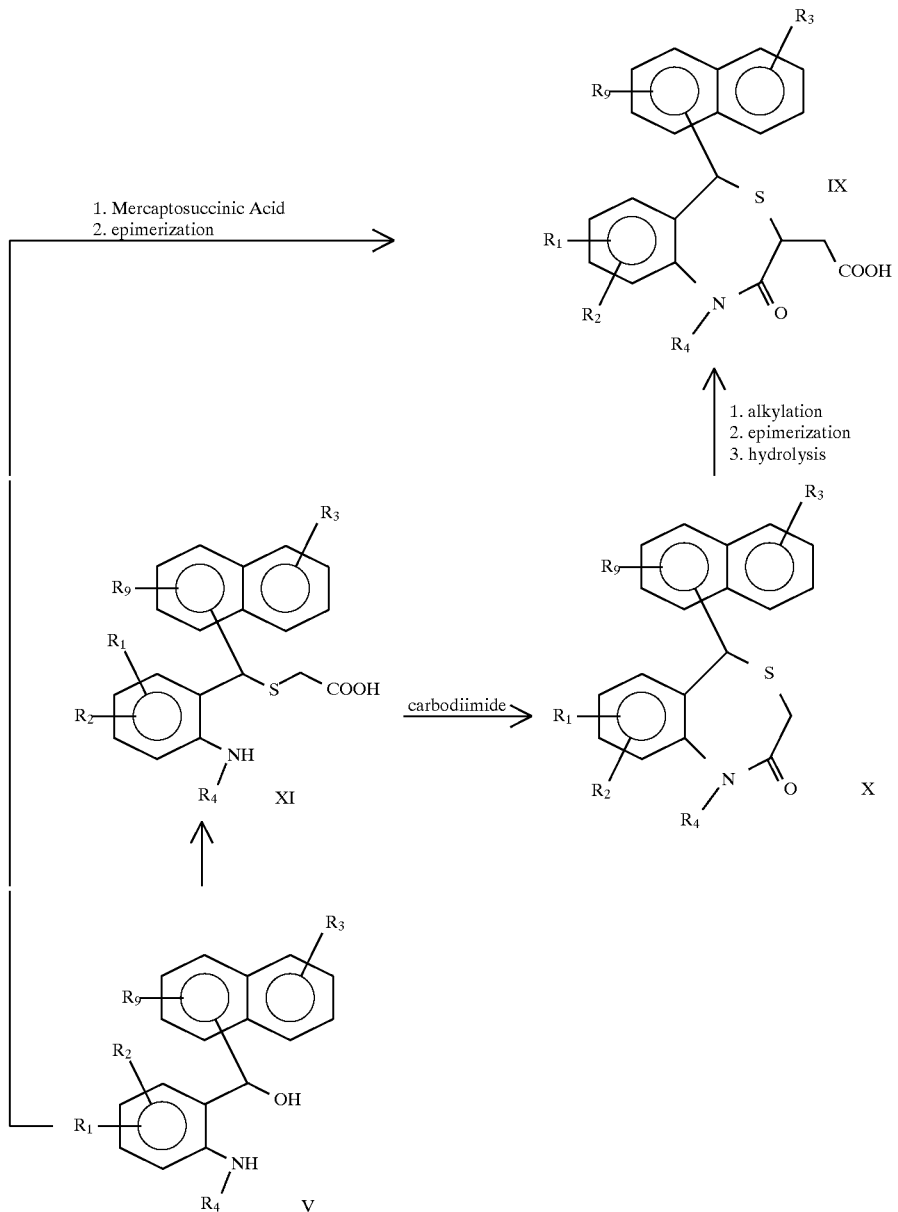

According to Reaction Scheme I the desired Formula ZQ compounds wherein $R_1$, $R_2$, $R_3$, $R_4$ and $R_9$ are as described above, X is oxy, Y is carbonyl or methylene and Z is a substituted amide (depicted as Formula II compounds) may be prepared by acylating the appropriate amine with the corresponding Formula III compound wherein Z is carboxyl.

Generally, the acid is combined with the appropriate amine in an aprotic solvent such as dimethylformamide in the presence of an amine base such as triethylamine and a coupling agent such as diethyl cyanophosphonate or propylphosphonic anhydride at a temperature of about 0° C. to about 40° C. for about 1 hour to about 6 hours.

Alternatively, the acid is combined with the appropriate amine in the presence of a carbodiimide (e.g., 1-(3-dimethylaminopropyl)-3-ethylcarbodiimide hydrochloride) in a reaction inert solvent such as methylene chloride at a temperature of about 10° C. to 40° C. for about 2 to about 24 hours.

The desired Formula ZQ compound wherein Z or V is tetrazol-5-yl may be prepared from the corresponding Formula I compound wherein Z or V is carboxyl by converting the carboxyl group to a carboxamide group (Z or V=$CONH_2$), dehydrating the carboxamide to the nitrile (Z or V=CN) and reacting the nitrile with an appropriate azide to form the tetrazole group.

Generally, the acid is converted to the imidazolide by reaction with carbonyl diimidazole in an aprotic solvent such as methylene chloride at a temperature of 15° C. to about 40° C. for about 30 minutes to about 4 hours, conveniently at room temperature for 1 hour. The resulting imidazolide is converted to the corresponding amide by bubbling ammonia gas into the reaction mixture at a temperature of 10° C. to about 40° C. for about 3 minutes to about 30 minutes, preferably at room temperature for about 5 minutes or until the reaction is complete by TLC analysis.

The amide is converted to the nitrile by treatment with trifluoroacetic anhydride and triethylamine in an inert solvent such as methylene chloride at 0° C. for about 25 minutes to 2 hours, preferably 30 minutes. Treatment of the nitrile with sodium azide and ammonium chloride in dimethylformamide at a temperature of about 90° C. to about 130° C. for about 7 hours to about 60 hours, preferably at a temperature of 120° C. for 24 hours, yields the desired tetrazole.

The desired Formula ZQ compound wherein Z or V is 4,5-dihydro-5-oxo-1,2,4-oxadiazol-3-yl may be prepared from the corresponding Formula ZQ compound wherein Z or V is CN by converting the nitrile to the amide oxime and reacting the amide oxime with a carbonylating agent to form the corresponding 4,5-dihydro-5-oxo-1,2,4-oxadiazole derivative.

Generally, the nitrile is converted to the amide oxime by reaction with hydroxylamine hydrochloride in the presence of a base such as potassium carbonate in an alcoholic solvent at a temperature of about 60° C. to about 110° C. for about 5 hours to 24 hours, preferably in refluxing ethanol for about 18 hours. The amide oxime is converted to the corresponding 4,5-dihydro-5-oxo-1,2,4-oxadiazole derivative by reaction with carbonyiduimidazole and triethylamine in refluxing ethyl acetate for 24 hours.

Prodrugs of Formula ZQ compounds having a carboxyl group may be prepared by combining the acid with the appropriate alkyl halide in the presence of a base such as potassium carbonate in an inert solvent such as dimethylformamide at a temperature of about 15° C. to about 100° C. for about 1 hour to about 24 hours.

Alternatively, the acid is combined with the appropriate alcohol as solvent in the presence of a catalytic amount of acid such as concentrated sulfuric acid at a temperature of about 20° C. to about 120° C., preferably at reflux, for about 1 hour to about 24 hours.

The desired Formula III compounds wherein $R_1$, $R_2$, $R_3$, $R_4$ and $R_9$ are as described above, X is oxy, Y is carbonyl or methylene and Z is carboxyl may be prepared from the corresponding Formula IV compound by cyclization followed by hydrolysis. Alternatively, the hydrolysis step may be omitted resulting in the desired prodrugs.

Generally, the Formula IV compound is combined with a base such as potassium carbonate in an alcoholic solvent such as ethanol at a temperature of about 10° C. to about 40° C., preferably ambient, for about 2 hours to about 18 hours followed by hydrolysis in an aqueous alcoholic solvent such as methanol/water with a base such as potassium carbonate at a temperature of about 40° C. to about 80° C., preferably at reflux, for about 2 hours to about 18 hours.

The desired Formula IV compounds wherein $R_1$, $R_2$, $R_3$, $R_4$ and $R_9$ are as described above, X is oxy, Y is carbonyl or methylene and P is a known carboxyl protecting group (see reference below) may be prepared from the appropriate corresponding Formula V compound by acylation or alkylation as appropriate.

Generally, for those compounds wherein Y is carbonyl the appropriate Formula V compound is combined with the appropriate fumaryl chloride protected mono acid, such as fumaryl chloride monoalkyl ester, in a reaction-inert solvent such as methylene chloride at a temperature of about 10° C. to about 50° C., typically ambient, for about six to about eighteen hours. Generally, for those compounds wherein Y is methylene the appropriate Formula V compound is combined with the appropriate protected 4-halocrotonic acid, such as alkyl 4-halocrotonate, in the presence of a base such as potassium carbonate in an aprotic solvent such as dimethylformamide at a temperature of about 10° C. to about 50° C., typically ambient, for about 12 hours to about 72 hours.

The desired Formula V compound wherein $R_1$, $R_2$, $R_3$, $R_4$ and $R_9$ are as described above may be prepared from the appropriate corresponding Formula VI compound by hydroxyalkylation (a modified Friedel-Crafts reaction).

Generally, the Formula VI compound is combined with a Lewis acid such as boron trichloride in a reaction-inert solvent such as benzene or toluene at a temperature of about ambient to about reflux for about 1 to about 6 hours under a nitrogen atmosphere to form an intermediate complex. The resulting complex is combined with the appropriately substituted naphthaldehyde in a reaction-inert solvent such as benzene in the presence of an amine base such as triethylamine at a temperature of about 0° C. to about 40° C., typically ambient, for about 30 minutes to about 18 hours followed by acid cleavage of the boron moiety.

Alternatively, a Formula V compound, wherein $R_1$ is 4-trifluoromethyl and $R_4$ is neopentyl, may be prepared by treating a Formula VI compound, wherein $R_1$ is 4-trifluoromethyl and $R_4$ is pivaloyl, with excess strong base, preferably 2.5 equivalents of n-butyllithium, in an anhydrous ethereal solvent, preferably tetrahydrofuran, at a temperature of about ambient to about 50° C. for about 1 hour to about 3 hours and reacting the resulting dianion with the appropriate naphthaldehyde. The resulting 2-(alpha-hydroxymethylnaphthalene) Formula V compound, wherein $R_4$ is pivaloyl, is converted to the Formula V compound, wherein $R_1$ is 4-trifluoromethyl and $R_4$ is neopentyl, by reducing the pivalamide functionality with a reducing agent such as lithium aluminum hydride or borane, preferably a borane-tetrahydrofuran complex, in an ethereal solvent such as tetrahydrofuran at an elevated temperature, typically reflux. Alternatively, the Formula V compounds wherein $R_1$ is 4-trifluoromethyl and $R_4$ is alkyl, including neopentyl, may be prepared by treating the Formula VI compound, wherein $R_1$ is 4-trifluoromethyl and $R_4$ is t-butoxycarbonyl, with an excess of t-butyllithium, preferably 2.4 equivalents, at a temperature of about –50° C. to about –0° C. in an ethereal solvent such as anhydrous tetrahydrofuran for about 2 hours to about 4 hours and coupling the resulting dianion with the appropriate naphthaldehyde. The resulting 2-(alpha-hydroxymethylnaphthalene) Formula V compound, wherein $R_1$ is 4-trifluoromethyl and $R_4$ is t-butoxycarbonyl, is treated with acid and thereby converted to the Formula V compound, wherein $R_1$ is 4-trifluoromethyl and $R_4$ is H. This compound is transformed to the Formula V compound, wherein $R_1$ is 4-trifluoromethyl and $R_4$ is alkyl, by reductive animation under conditions similar to that for the preparation of the Formula VI compounds.

The desired Formula VI compound wherein $R_1$, $R_2$ and $R_4$ are as described above may be prepared from the appropriate corresponding aniline by reductive animation.

Generally, the aniline is reacted with the appropriate alkylaldehyde in a protic acidic solvent such as concentrated acetic acid at a temperature of about 10° C. to about 50° C., preferably ambient, for about 30 minutes to about four hours followed by reduction using for example sodium borohydride at a temperature of about 0° C. to about 20° C. for about 15 minutes to about four hours.

Alternatively, the aniline is reacted with the appropriate alkylaldehyde in an aprotic solvent such as 1,2-dichloroethane in the presence of an acid such as acetic acid at a temperature of about 15° C. to about 40° C., preferably ambient temperature, for a period of about 1 to about 20 hours followed by reduction using for example sodium triacetoxyborohydride at about −20° C. to about ambient temperature for a period of about 1 to about 20 hours.

According to Reaction Scheme II the desired Formula VII compounds wherein $R_1$, $R_2$, $R_3$, $R_4$ and $R_9$ are as described above, X is thio, Y is carbonyl or methylene and Z is a substituted amide may be prepared by acylating the appropriate amine with the corresponding Formula VII or IX compound wherein Z is carboxyl. Generally this reaction may be performed as describe above for the Formula II compounds.

The desired Formula VI compounds wherein $R_1$, $R_2$, $R_3$, $R_4$ and $R_9$ are as described above, X is thio, Y is methylene may be prepared from the appropriate corresponding Formula IX compound where Y is carbonyl by a sequential reduction/oxidation procedure.

Generally the Formula IX compound is fully reduced using for example a borane-methyl sulfide complex in a reaction-inert solvent such as tetrahydrofuran at a temperature of about 20° C. to about 80° C., preferably at reflux, for about 1 hour to about 6 hours. The resulting alcohol is then oxidized to the Formula VIII compound using for example a two step procedure involving first a Swern oxidation followed by oxidation with buffered sodium chlorite in acetonitrile and aqueous hydrogen peroxide at a temperature of about −10° C. to about 25° C. for about 30 minutes to about 4 hours. Or alternatively, the alcohol is directly oxidized to the acid using t-butyl hydroperoxide and cetyl trimethyl ammonium sulfate in an aqueous mixture at pH>13.

The desired Formula IX compound wherein $R_1$, $R_2$, $R_3$, $R_4$ and $R_9$ are as described above, may be prepared from the appropriate corresponding Formula X compound by alkylation followed by epimerization and finally hydrolysis.

Generally, the Formula X compound is combined with a base such as lithium diisopropylamide in a reaction-inert solvent such as cyclohexane/tetrahydrofuran at a temperature of about −100° C. to about −20° C. under nitrogen for about 30 minutes to about 3 hours followed by addition of a suitable alkyl haloacetate such as t-butyl bromoacetate and mixing for about 2 to about 24 hours at a temperature of about 10° C. to about 40° C., preferably ambient. The alkylated product is epimerized to exclusively the trans isomers using a base like potassium carbonate in an alcoholic solvent like methanol for 1 hour to 6 hours at a temperature of about 40° C. to about 80° C., preferably at 60° C. The resulting t-butyl ester may be hydrolyzed by treatment with an acid such as trifluoroacetic acid in a reaction-inert solvent such as dichloromethane.

The desired Formula X compound wherein $R_1$, $R_2$, $R_3$, $R_4$ and $R_9$ are as described above, may be prepared from the appropriate corresponding Formula XI compound by coupling under carbodiimide conditions.

Generally, the Formula XI compound is combined with a suitable carbodiimide such as 1-(3-dimethylaminopropyl)-3-ethylcarbodiimide hydrochloride in a reaction-inert solvent such as dichloromethane at a temperature of about 10° C. to about 50° C., conveniently at ambient temperature, for about 5 hours to about 24 hours.

The desired Formula XI compound wherein $R_1$, $R_2$, $R_3$, $R_4$ and $R_9$ are as described above, may be prepared from the appropriate corresponding Formula V compound by a solvolytic displacement reaction.

Generally, the Formula V compound may be combined with mercaptoacetic acid under aqueous acidic conditions at a temperature of about 60° C. to about 120° C., conveniently at reflux, for about 2 to about 6 hours.

Alternatively, the desired Formula IX compounds wherein $R_1$, $R_2$, $R_3$, $R_4$, and $R_9$ are as described above may be prepared from the appropriate corresponding Formula V compound by a solvolytic displacement reaction with cyclization to the lactam followed by epimerization.

Generally, the Formula V compound and mercaptosuccinic acid are combined in a carboxylic acid solvent such as propionic acid and heated to about 100° C. to about 140° C. for about 12 to 72 hours with a means to remove water such as a nitrogen sweep across the head space of the reaction vessel. The cyclized product is epimerized to exclusively the trans isomers by treatment in an inert solvent such as tetrahydrofuran with a base such as a metal alkoxide base in the corresponding alcohol solvent, preferably sodium methoxide in methanol, at about ambient temperature to reflux temperature for a period of about 1 to about 24 hours.

The starting materials and reagents for the above described reaction schemes (e.g., 4-haloaniline, 1-naphthaldehyde, furmaric acid monoethyl ester, amino acid esters, prodrug residues, protected forms) are readily available or can be easily synthesized by those skilled in the art using conventional methods of organic synthesis.

Some of the preparation methods described herein will require protection of remote functionality (i.e., carboxyl). The need for these protecting groups will vary depending on the nature of the remote functionality and the conditions of the preparation methods. This need is readily determined by one skilled in the art. For a general description of protecting groups (e.g., halo($C_1$–$C_4$)alkyl, ($C_1$–$C_4$)alkoxymethyl, arylmethyl and tri($C_1$–$C_4$)alkylsilyl) and their use, see T. W. Greene, *Protective Groups in Organic Synthesis*, John Wiley & Sons, New York, 1991.

The compounds of Formula ZQ have asymmetric carbon atoms and therefore are enantiomers or diastereomers. Diasteromeric mixtures can be separated into their individual diastereomers on the basis of their physical chemical differences by methods known per se., for example, by chromatography and/or fractional crystallization. Enantiomers (e.g., of Formula III, VII or IX) can be separated by converting the enantiomeric mixture into a diasteromeric mixture (e.g., ester or salt) by reaction with an appropriate optically active compound (e.g., alcohol or amine), separating the diastereomers and converting (e.g., hydrolyzing or acidifying) the individual diastereomers to the corresponding pure enantiomers. All such isomers, including diastereomers and enantiomers are considered as part of this invention.

Some of the compounds of this invention, where for example Z contains an acid group, are acidic and they form a salt with a pharmaceutically acceptable cation. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

Some of the compounds of this invention where, for example Y is methylene or Z contains an amine group are basic, and they form a salt with a pharmaceutically acceptable anion. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, when the compounds of this invention form hydrates or solvates they are also within the scope of the invention.

Any squalene e

Any squalene epoxidase inhibitor may be used as the second compound of this invention. The term squalene epoxidase inhibitor refers to compounds which inhibit the bioconversion of squalene and molecular oxygen into squalene-2,3-epoxide, catalyzed by the enzyme squalene epoxidase. Such inhibition is readily determined by those skilled in the art according to standard assays (Biochim. Biophys. Acta 1984; 794:466–471). A variety of these compounds are described and referenced below however other squalene epoxidase inhibitors will be known to those skilled in the art. U.S. Pat. Nos. 5,011,859 and 5,064,864 (the disclosures of which are incorporated by reference) disclose fluoro analogs of squalene. EP publication 395,768 A (the disclosure of which is incorporated by reference) discloses substituted allylamine derivatives. PCT publication WO 9312069 A (the disclosure of which is hereby incorporated by reference) discloses certain amino alcohol derivatives. U.S. Pat. No. 5,051,534 (the disclosure of which is hereby incorporated by reference) discloses cyclopropyloxy-squalene derivatives.

Any squalene cyclase inhibitor may be used as the second component of this invention. The term squalene cyclase inhibitor refers to compounds which inhibit the bioconversion of squalene-2,3-epoxide to lanosterol, catalyzed by the enzyme squalene cyclase. Such inhibition is readily determined by those skilled in the art according to standard assays (FEBS Lett. 1989;244:347–350.). In addition, the compounds described and referenced below are squalene cyclase inhibitors, however other squalene cyclase inhibitors will also be known to those skilled in the art. PCT publication 9410150 (the disclosure of which is hereby incorporated by reference) discloses 1,2,3,5,6,7,8,8α-octahydro-5,5,8α (beta)-trimethyl-6-isoquinolineamine derivatives, such as N-trifluoroacetyl-1,2,3,5,6,7,8,8α-octahydro-2-allyl-5,5,8α (beta)-trimethyl-6(beta)-isoquinolineamine. French publication 2697250 (the disclosure of which is hereby incorporated by reference) discloses beta, beta-dimethyl-4-piperidine ethanol derivatives such as 1-(1,5,9-trimethyldecyl)-beta, beta-dimethyl-4-piperidineethanol.

Any combined squalene epoxidase/squalene cyclase inhibitor may be used as the second component of this invention. The term combined squalene epoxidase/squalene cyclase inhibitor refers to compounds that inhibit the bioconversion of squalene to lanosterol via a squalene-2,3-epoxide intermediate. In some assays (certain experimental conditions) it is not possible to distinguish between squalene epoxidase inhibitors and squalene cyclase inhibitors, however, these assays (experimental conditions) are recognized by those skilled in the art. Thus, inhibition by combined squalene epoxidase/squalene cyclase inhibitors is readily determined by those skilled in art according to the aforementioned standard assays for squalene cyclase or squalene epoxidase inhibitors. A variety of these compounds are described and referenced below however other squalene epoxidase/squalene cyclase inhibitors will be known to those skilled in the art. U.S. Pat. Nos. 5,084,461 and 5,278,171 (the disclosures of which are incorporated by reference) disclose azadecalin derivatives. EP publication 468,434 (the disclosure of which is incorporated by reference) discloses piperidyl ether and thio-ether derivatives such as 2-(1-piperidyl)pentyl isopentyl sulfoxide and 2-(1-piperidyl)ethyl ethyl sulfide. PCT publication WO 9401404 (the disclosure of which is hereby incorporated by reference) discloses acyl-piperidines such as 1-(1-oxopentyl-5-phenylthio)-4-(2-hydroxy-1-methyl)-ethyl) piperidine. U.S. Pat. No. 5,102,915 (the disclosure of which is hereby incorporated by reference) discloses cyclopropyloxy-squalene derivatives.

Any lanosterol demethylase inhibitor may be used as the second compound of this invention. The term lanosterol demethylase inhibitor refers to compounds which inhibit the 14-demethylation of lanosterol catalyzed by the enzyme lanosterol demethylase. Such inhibition is readily determined by those skilled in the art according to standard assays (Biochemistry 1994; 33:4702–4713 and references cited therein). A variety of these compounds are described and referenced below however other lanosterol demethylase inhibitors will be known to those skilled in the art. U.S. Pat. Nos. 4,782,059 and 4,894,375 (the disclosures of which are hereby incorporated by reference) disclose azoles such as cis-1-acetyl 4-(4-((2-(2,4-dichlorophenyl)-2-(1H-imidazol-1-ylmethyl) 1,3-dioxolan-4-yl)methoxy)phenyl)piperazine (ketoconazole). EP publication 492474A (the disclosure of which is hereby incorporated by reference) discloses novel dioxolanes such as (2S,4S)-Cis-2-(2-(4-chlorophenyl)ethyl) -2-imidazol-1 -yl) methyl-4-(4-aminophenyl-thio)methyl-1, 3-dioxolane. U.S. Patent No. 5,041,432 (the disclosure of which is hereby incorporated by reference) discloses 15-substituted lanosterol derivatives.

The pharmaceutical combinations of this invention are all adapted to therapeutic use as agents that lower plasma LDL cholesterol levels in mammals, particularly humans. Since the concentration of cholesterol in blood is closely related to the development of cardiovascular, cerebral vascular or peripheral vascular disorders, these combinations, by virtue of their hypolipidemic action, prevent, arrest and/or regress atherosclerosis.

The hypercholesterolemia controlling activity of these compounds in animals may be demonstrated by methods based on standard procedures. For example, the in vivo activity of these compounds in lowering cholesterol levels may be determined by a procedure similar to that described by Harwood et al., (J. Lip. Res. 1993 34:377–95). Activity (and thus dosages) can be determined by the amount of combination hypocholesterolemic agent of this invention that reduces cholesterol levels, relative to the control, in male golden Syrian hamsters. Male golden Syrian hamsters are administered either a cholesterol-free semi-purified powdered diet (AIN-76C) (control animals) or the same cholesterol-re semi-purified powdered diet supplemented with the cholesterol absorption inhibitor and cholesterol synthesis inhibitor combination of this invention. The hamsters are housed in cages containing six animals and are fed the diet for seven days. Hamster feces are collected over a period of one to two days at the end of the treatment period. At the end of the seven days, following anesthesia, blood is drawn for the determination of plasma cholesterol concentrations.

Total plasma cholesterol is analyzed spectrophotometrically using a commercial assay kit (SingleVial, Boehringer Mannheim, Indianapolis, Ind.) based on cholesterol oxidase production of $H_2O_2$ after hydrolysis of cholesterol esters by cholesterol esterase, the details of which are described in full in the Examples hereinafter.

High density lipoprotein (HDL)-cholesterol is measured after precipitation of apolipoprotein B-containing particles by a method described by Assmann et al. (Clin. Chem. 1983; 29:2026–30), the details of which are described in full in the Examples hereinafter.

Non-HDL cholesterol (a combination of LDL-cholesterol, IDL-cholesterol, VLDL-cholesterol and chylomicron-derived cholesterol) is calculated by subtracting the HDL-cholesterol concentration from the total plasma cholesterol (both of which are described in the preceding paragraphs).

Fecal neutral sterols are analyzed by gas liquid chromatography by modifications of methods described by Miettinen (Clin. Chim. Acta. 1982; 124:245–8) and by Harris et al (Clin. Pharmacol. Ther. 1990; 48:189–94), the details of which are described in full in the Examples hereinafter.

HMG-CoA reductase activity is measured in microsomal fractions isolated from homogenates of liver tissue by differential centrifugation by a method described in full in the Examples hereinafter.

Anti-atherosclerosis effects of the compounds (i.e., combination activity and thus dosages) can be determined by the amount of combination agent of this invention that reduces the lipid deposition, relative to the control, in the aortas of New Zealand White rabbits. Male New Zealand White rabbits are pre-fed a diet containing 40 mg/kg cholesterol and 1 gm/kg peanut oil for 3–5 days (meal-fed once a day) and then bled for total plasma cholesterol measurement. Rabbits are assigned to groups based on their plasma cholesterol response to the dietary cholesterol challenge so that the means and standard deviations of each group are similar. To examine the effects of the combination therapy on atherosclerosis progression, groups of rabbits are fed the cholesterol-peanut oil diet (control) or the same diet with the combination agent of this invention for 12 weeks. Alternatively, to assess the effect of this invention on the regression of atherosclerosis, New Zealand White rabbits can be fed the cholesterol-peanut oil diet described above, assigned to treatment groups with continued feeding for 6 to 10 months. At that point, rabbits are switched to a diet containing no cholesterol nor peanut oil (control) or the same diet with the combination agent of this invention for up to 6 months. At the end of the treatment period of either protocol the animals are euthanitized, and the aortas removed from the thoracic arch to the branch of the iliacs. The aortas are cleaned of adventitia, opened longitudinally and split in two equal pieces. Reduced lipid deposition in the rabbits given the combination agent of this invention relative to the control animals can be determined through lipid analysis of aorta for cholesterol and cholesteryl ester and/or by lipid staining and analysis using an image analyzer.

Administration of the combination compounds of this invention can be via any method which delivers the cholesterol absorption inhibitor to the intestinal lumen and the cholesterol biosynthesis inhibitor to the intestine and the liver. These methods include oral routes, intraduodenal routes etc.

The two different compounds of this invention can be co-administered simultaneously or sequentially in any order, or a single pharmaceutical composition comprising a cholesterol absorption inhibitor and a cholesterol synthesis inhibitor in a pharmaceutically acceptable carrier can be administered. Thus, for example, in one mode of administration a cholesterol absorption inhibitor may be administered two to three times a day with meals and a cholesterol synthesis inhibitor (e.g., HMG-CoA reductase inhibitor) may be administered once at night prior to sleep. Alternatively the two compounds may be administered simultaneously (once, twice or three times daily with or without meals). In any event the amount and timing of compounds administered will, of course, be dependent on the subject being treated, on the severity of the affliction, on the manner of administration and on the judgement of the prescribing physician. The following paragraphs provide preferred dosage ranges for the various components of this invention.

An effective dosage for the cholesterol absorption inhibitors described above is in the range of 0.001 to 20 mg/kg/day, preferably 0.005 to 10 mg/kg/day, most preferably 0.01 to 5 mg/kg/day. For an average 70 kg human, this would amount to 0.00007 to 1.4 g/day, preferably 0.00035 to 0.7 g/day, most preferably 0.0007 to 0.35 g/day.

In general an effective dosage for the cholesterol synthesis inhibitors described above is in the range of 0.00001 to 20 mg/kg/day, preferably 0.00005 to 10 mg/kg/day, most preferably 0.00007 to 4 mg/kg/day. For an average 70 kg human, this would amount to 0.000007 to 1.4 g/day, preferably 0.0000035 to 0.7 g/day, most preferably 0.000005 to 0.28 g/day.

In particular, an effective dosage for the HMG-CoA reductase inhibitors is in the range of 0.00001 to 20 mg/kg/day, preferably 0.00005 to 2 mg/kg/day. For an average 70 kg human, this would amount to 0.0000007 to 1.4 g/day, preferably 0.0000035 to 0.14 g/day.

Most preferably, the dose range for lovastatin is 0.07 to 1.14 mg/kg/day, and for an average 70 kg human, this would amount to approximately 0.005 to 0.08 g/day.

Most preferably, the dose range for simvastatin is 0.014 to 0.6 mg/kg/day, and for an average 70 kg human, this would amount to approximately 0.001 to 0.04 g/day. Most preferably, the dose range for pravastatin is 0.035 to 0.57 mg/kg/day, and for an average 70 kg human, this would amount to approximately 0.0025 to 0.04 g/day. Most preferably, the dose range for fluvastatin is 0.07 to 0.57 mg/kg/day, and for an average 70 kg human, this would amount to approximately 0.005 to 0.04 g/day. Most preferably, the dose range for atorvastatin is 0.0071 to 1.14 mg/kg/day, and for an average 70 kg human, this would amount to approximately 0.0005 to 0.08 g/day.

Most preferably, the dose range for rivastatin is 0.00071 to 0.14 mg/kg/day, and for an average 70 kg human, this would amount to 0.00005 to 0.01 g/day.

An effective dosage for the HMG-CoA synthase inhibitors is in the range of 0.285 to 28.57 mg/kg/day, preferably 0.285 to 5 mg/kg/day. For an average 70 kg human, this would amount to 0.020 to 2 g/day, preferably 0.020 to 0.35 g/day.

An effective dosage for inhibitors of HMG-CoA reductase gene expression is in the range of 0.005 to 20 mg/kg/day, preferably 0.01 to 10 mg/kg/day, most preferably 0.01 to 5 mg/kg/day. For an average 70 kg human, this would amount to 0.00035 to 1.4 g/day, preferably 0.0007 to 0.7 g/day, most preferably 0.0007 to 0.35 gm/day.

An effective dosage for the squalene synthetase inhibitors is in the range of 0.005 to 20 mg/kg/day, preferably 0.01 to 10 mg/kg/day, most preferably 0.01 to 5 mg/kg/day. For an average 70 kg human, this would amount to 0.00035 to 1.4 g/day, preferably 0.0007 to 0.7 g/day, most preferably 0.0007 to 0.35 gm/day.

An effective dosage for the squalene epoxidase inhibitors is in the range of 0.005 to 20 mg/kg/day, preferably 0.01 to 10 mg/kg/day, most preferably 0.01 to 5 mg/kg/day. For an average 70 kg human, this would amount to 0.00035 to 1.4 g/day, preferably 0.0007 to 0.7 g/day, most preferably 0.0007 to 0.35 gm/day.

An effective dosage for the squalene cyclase inhibitors is in the range of 0.005 to 20 mg/kg/day, preferably 0.01 to 10 mg/kg/day, most preferably 0.01 to 5 mg/kg/day. For an average 70 kg human, this would amount to 0.00035 to 1.4 g/day, preferably 0.0007 to 0.7 g/day, most preferably 0.0007 to 0.35 gm/day.

An effective dosage for combined squalene cyclase/squalene epoxidase inhibitors is in the range of 0.005 to 20 mg/kg/day, preferably 0.01 to 10 mg/kg/day, most preferably 0.01 to 5 mg/kg/day. For an average 70 kg human, this would amount to 0.00035 to 1.4 g/day, preferably 0.0007 to 0.7 g/day, most preferably 0.0007 to 0.35 gm/day.

An effective dosage for the lanosterol demethylase inhibitors is in the range of 0.005 to 20 mg/kg/day, preferably 0.01 to 5 mg/kg/day. For an average 70 kg human, this would amount to 0.00035 to 1.4 g/day, preferably 0.0007 to 0.35 g/day.

The compounds can be administered individually or together in any conventional oral or parenteral dosage form such as a capsule, tablet, powder, cachet, suspension or solution. For oral administration, which is preferred, a pharmaceutical composition can take the form of solutions, suspensions, tablets, pills, capsules, powders, and the like.

Depending on the intended mode of administration, the pharmaceutical compositions may be in the form of solid, semi-solid or liquid dosage forms, such as, for example, tablets, pills, capsules, powders, liquids, suspensions, or the like, preferably in unit dosage forms suitable for single administration of precise dosages. The pharmaceutical compositions will include a conventional pharmaceutical carrier or excipient and a compound(s) according to the invention as an active ingredient. In addition, it may include other medicinal or pharmaceutical agents, carriers, adjuvants, etc.

Pharmaceutical compositions according to the invention may contain 0.1 %–95% of the compound(s) of this invention, preferably 1%–70%. In any event, the composition or formulation to be administered will contain a quantity of a compound(s) according to the invention in an amount effective to alleviate the signs of the subject being treated, i.e., hypercholesterolemia or atherosclerosis.

For solid pharmaceutical compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like.

Liquid pharmaceutically administrable compositions can be prepared by dissolving or dispersing, or otherwise preparing a compound(s) according to this invention and mixing it optionally with a pharmaceutical adjuvant in a carrier, such as, for example, water, saline, aqueous dextrose, glycerol, ethanol, and the like, to thereby form a solution or suspension.

Methods of preparing various pharmaceutical compositions with a certain amount of active ingredient are known, or will be apparent, to those skilled in this art. For examples, see Remington's Pharmaceutical Sciences., Mack Publishing Company, Easter, Pa., 15th Edition (1975).

Since the present invention relates to the reduction of plasma cholesterol levels by treatment with a combination of active ingredients which may be administered separately, the invention also relates to combining separate pharmaceutical compositions in kit form. The kit includes two separate pharmaceutical compositions: a cholesterol synthesis inhibitor and a cholesterol absorption inhibitor. The kit includes container means for containing the separate compositions such as a divided bottle or a divided foil packet. Typically the kit includes directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

The following EXAMPLES demonstrate that neither of the cholesterol absorption inhibitors, (3β, 5α, 25R)-3-((β-D-cellobiosyl)oxy)spirostan-11-one or tigogenin cellobioside (tiqueside, described in U.S. Pat No. 4,602,003) is able to decrease plasma cholesterol concentrations in hamsters fed a cholesterol4ree diet. Surprisingly, the combination of a cholesterol absorption inhibitor and a cholesterol synthesis inhibitor results in a decrease in total plasma cholesterol and specifically plasma non-HDL cholesterol levels. The effect of combination therapy is confined to the non-HDL fractions; there is no effect on HDL cholesterol concentrations. This is important because HDL has been shown in multiple epidemiological studies to be a negative risk factor for cardiovascular disease.

The cholesterol absorption inhibitor (3β, 5α, 25R)-3-((β-D-cellobiosyl)oxy)spirostan-11-one also increases fecal neutral sterol excretion. Surprisingly, this cholesterol absorption inhibitor in combination with a cholesterol synthesis inhibitor, results in additional fecal neutral sterol excretion. Although there are several reports in the literature that cholesterol synthesis inhibitors inhibit cholesterol absorption in vivo or cholesterol uptake in cell culture, there is no effect of lovastatin alone on fecal neutral sterol excretion in hamsters, thus the increase in fecal neutral sterol excretion for these combinations is unexpected.

Hepatic microsomal HMG-CoA reductase activity detailed in the following Examples is a measure of total HMG-CoA reductase enzyme present, and is a marker for the perturbation of liver cholesterol metabolism by hypolipidemic therapy. HMG-CoA is the major regulatory step in cholesterol biosynthesis, and increased expression of HMG-CoA reductase protein occurs following hypolipidemic therapy. There is species variability in the extent to which induction can occur and it is believed that there is an upper limit to that induction. It is believed that combination therapy of a cholesterol absorption inhibitor and a cholesterol biosynthesis inhibitor causes greater perturbations of hepatic cholesterol metabolism than with either agent alone, and results in maximal or near maximal increases in HMG-CoA reductase protein levels as well as lowering of plasma LDL-cholesterol which does not occur with either agent alone.

It is believed that the hamster represents a suitable animal model to demonstrate this invention. However, hepatic regulation of cholesterol metabolism in the hamster is somewhat different than in man. This is believed because known HMG-CoA reductase inhibitors that are hypolipidemic in man are not hypolipidemic in monotherapy in hamsters fed a cholesterol-free diet. It is believed that the degree to which HMG-CoA reductase can be induced, and thus resulting cholesterol synthesis, in response to hypolipidemic therapy is greater in the hamster than in man. It is also believed that the hamster preferentially induces HMG-CoA reductase over up regulation of LDL-receptor whereas in man both are believed to occur. It is the up regulation of LDL-receptor and the resulting increase clearance of LDL-cholesterol that leads to plasma cholesterol lowering. Thus, it is believed that in man, monotherapy with either a cholesterol absorption inhibitor or a cholesterol synthesis inhibitor will lower plasma LDL-cholesterol, but the addition of the second agent will provide additional hypolipidemic activity.

EXAMPLE 1

A four day study of the combination of tigogenin cellobioside and lovastatin (given by diet admix) on plasma cholesterol levels and hepatic HMG-CoA reductase activity in hamsters fed a cholesterol-free diet was performed according to the Methods detailed at the end of the EXAMPLES. The data is detailed below.

| Treatment | | Total Plasma Cholesterol (mg/dl) | HMG-CoA Reductase Act. (pmol/min/mg) |
|---|---|---|---|
| Control | | 151 ± 28 | 58 ± 5 |
| lovastatin | @ 0.025% | 140 ± 17 | 124 ± 9 |
| | @ 0.05% | 130 ± 9 | 134 ± 12 |
| | @ 0.1% | 129 ± 7 | 569 ± 14 |
| tiqueside | @ 0.1% | 149 ± 18 | 78 ± 5 |
| +lovastatin | @ 0.025% | 145 ± 7 | 553 ± 31 |
| | @ 0.05% | 130 ± 7 | 587 ± 5 |
| | @ 0.1% | 113 ± 9 | 1270 ± 33 |

EXAMPLE 2

A seven day study of the combination of 0.2% (3α,5α, 25R)-3-((β-D-cellobiosyl)oxy)spirostan-11-one (hereinafter referred to in the Examples as Compound A) with lovastatin (given by diet admix) on plasma cholesterol levels in hamsters fed a cholesterol-free diet was performed according to the Methods detailed at the end of the EXAMPLES. The data is detailed below.

| Plasma non-HDL cholesterol levels (in mg/dl). | |
|---|---|
| Control | 27 ± 9 |
| +lovastatin | |
| 0.05% | 15 ± 7 |
| 0.1% | 32 ± 19 |
| 0.2% | 38 ± 22 |
| +Compound A @ 0.2% | 24 ± 11 |
| +lovastatin | |
| 0.05% | 8 ± 5 |
| 0.1% | 1 ± 8 |
| 0.2% | −2 ± 1 |

EXAMPLE 3

A seven day study of the combination of Compound A and lovastatin given by diet admix in hamsters fed a cholesterol-ree diet was performed according to the Methods detailed at the end of the EXAMPLES. The data are detailed below.

| Treatment | | Non-HDL-Cholesterol (mg/dl) | Fecal Neutral Sterols (mg/gm feces) | HMG-CoA reductase (pmol/min/mg) |
|---|---|---|---|---|
| Control | | 51 ± 9 | 3.43 | 51 ± 21 |
| Compound A | @ 0.2% | 52 ± 23 | 16.5 | 773 ± 276 |
| +lovastatin | @ 0.025%, | 14 ± 28 | 23.8 | 1515 ± 276 |
| | @ 0.05% | 10 ± 11 | 37.2 | 1443 ± 527 |
| | @ 0.1% | −15 ± 12 | 48.5 | 1929 ± 48 |
| lovastatin | @ 0.1% | 69 ± 24 | 2.86 | 302 ± 250 |
| +Compound A | @ 0.05% | 44 ± 18 | 28.4 | 1505 ± 164 |
| | @ 0.1% | 24 ± 16 | 30.9 | 1340 ± 462 |
| | @ 0.2% | 20 ± 10 | 47.1 | 1746 ± 129 |

METHODS

Animals: Male Syrian Golden hamsters were fed a semi-purified powdered diet (AIN-76C diet) containing no cholesterol. Cholesterol absorption inhibitor and/or cholesterol synthesis inhibitor were administered as diet admix. Hamsters were housed in cages containing 6 animals and were fed the diet for 4–7 days. Following anesthesia, blood was drawn for the determination of plasma cholesterol concentrations and other tissues and feces were collected occasionally.

Measurement of Plasma Lipid Concentrations

Total Plasma Cholesterol (TPC): Whole blood was collected into tubes containing lithium heparin. Plasma was isolated by centrifuging the samples at ⁻1500×g for 25 min. Plasma samples were analyzed for TPC using a commercial assay kit (SingleVial, Boehringer Mannheim, Indianapolis, Ind.) based on cholesterol oxidase production of H after hydrolysis of cholesterol esters by cholesterol esterase. Fifteen microliter samples were placed into a 96-well plate (triplicate assay wells) and 200 $\mu$l of "cholesterol reagent" was added. One hour later, the intensity of the developed color was measured at 490 nm using a 96-well plate spectrophotometer (Molecular Devices, Menlo Park, Calif.). Absorbance was converted into concentration (mg/dl) by comparison with a standard curve constructed concurrently from standards supplied with the kit.

High Density Lipoprotein-Cholesterol: HDL-cholesterol was measured after precipitation of apolipoprotein B-containing particles by method described by Assmann et al. (Clin Chem 1983; 29:2026–30). Briefly, one volume of plasma (usually 75 $\mu$l) was mixed with two volumes of phosphotungstic acid:MgCl2 (1.06 g/L:25 mM). Samples were mixed thoroughly and then centrifuged at 1500×g for 10 min. The cholesterol remaining in the supernatant was then measured exactly as described above for total plasma cholesterol. The calculated concentration was then multiplied by 3 to correct for the dilution that occurred due to addition of precipitation reagent.

Non-HDL-Cholesterol: Non-HDL-cholesterol (a combination of LDL-cholesterol, IDL-cholesterol, VLDL-cholesterol, and chylomicron-derived cholesterol) was calculated by subtracting the HDL-C concentration from the TPC concentration.

Measurement of Fecal Neutral Sterol Excretion: Fecal neutral sterols were analyzed by gas liquid chromatography (GLC) by modifications of methods described by Miettinen (Clin Chim Acta. 1982; 124:245–8) and by Harris et al (Clin Pharmacol Ther 1990; 48:189–94). Hamster feces were collected from hamsters housed 6 per cage over a period of 1–2 days at the end of the study period. The feces were lyophilized to constant weight and then were pulverized to homogeneity using ball bearings in plastic vials with a paint shaker and were stored at −20° C. until use.

Fifty milligrams of lyophilized powdered feces were saponified in 2 ml of 1N NaOH in 90% ethanol at 80° C. for 1 hour. 5α-Cholestane (50 or 100 $\mu$g/50 mg sample) was added prior to saponification as an internal recovery standard. After adding 1 ml of water to the saponified mixture, neutral sterols were extracted 3 times with 5 ml of petroleum ether. The pooled extracts were dried under nitrogen, and trimethylsilyl (TMS) ethers were prepared by adding 0.5 ml of pyridine:hexamethyidisilazane: trimethylchlorosilane (9:3:1) for 30 min at room temperature. The mixture was dried under desiccated nitrogen, and the TMS ethers of the sterols were resuspended in 200 $\mu$l of ethyl acetate for GLC injection. GLC was performed on 60 m×0.32 mM inner diameter glass capillary SPB-1 column (Supelco, Bellefonte, Pa.) using a temperature program of 20° C./min from 190° C. to 265° C. (Varian Vista 6000, Walnut Creek, Calif.). Sterol analyses were performed in triplicate except where insufficient recovery of feces occurred. Purified coprostanol, cholestanol, cholesterol, coprostanone and β-sitosterol were used to identify the neutral sterols by comparison of retention times. Quantitation of neutral sterols was accomplished by comparing the relative peak areas (normalized to 5α-cholestane) of the hydrogen flame ionization detector response to that obtained from known amounts of purified standards.

Measurement of HMG-CoA Reductase Activity: The assay for HMG-CoA reductase activity was performed as described by Harwood et al. (J Lip Res 1993; 34:377–95). Briefly, hepatic microsomes were prepared by homogenizing 0.5–1.0 g pieces of liver immediately upon removal from the animal using 15 strokes of a Dounce tissue homogenizer at 4° C. in TEDK buffer [50 mM Tris (pH 7.5), 1 mM EDTA, 5 mM dithiothreitol, 70 mM KCl; 2 ml per g liver]. Homogenates were first centrifuged at 4° C. for 20 min at 10,000×g and the supernatants were further centrifuged at 4° C. for 90 min at 178,000×g. The resulting microsomal pellets were resuspended in 1 ml TEDK buffer per g liver by five strikes of a Potter-Elvehjem pestle and were stored frozen in liquid $N_2$. Microsomal protein (150 µg) was incubated for 30 min at 37° C. in a final volume of 75 µl TEDK buffer that contained 3.4 mM NADP+, 30 mM glucose-6-phosphate, 0.2 U glucose-6-phosphate dehydrogenase, 66.7 µM HMG-CoA (spiked with [14] HMG-CoA, final specific activity 10 cpm/pmol), 15,000–20,000 cpm [$3^H$]mevalonate (0.6–1.2 Ci/mmol; used as an internal standard), and 68 mM EDTA to prevent conversion of mevalonate to phosphomevalonate during the incubation. Following incubation, 10 ml of 6N HCl were added to terminate the enzymatic reaction and to convert the newly formed mevalonate into mevalonolactone. The mevalonolactone was then separated from unreacted substrate by silica gel thin layer chromatography developed in toluene-:acetone 1:1. The separated mevalonolactone (Rf=0.4–1.0) was then counted for radioactivity in a liquid scintillation counter. HMG-CoA reductase activity is expressed as pmol of mevalonate formed from HMG-CoA per min per mg of microsomal protein.

It should be understood that the invention is not limited to the particular embodiments described herein, but that various changes and modifications may be made without departing from the spirit and scope of this novel concept as defined by the following claims.

What is claimed is:

1. A pharmaceutical combination composition comprising: a. a therapeutically effective amount of a first compound, said first compound being a cholesterol absorption inhibitor selected from Group I and Group II wherein GROUP I
comprises a compound of Formula I

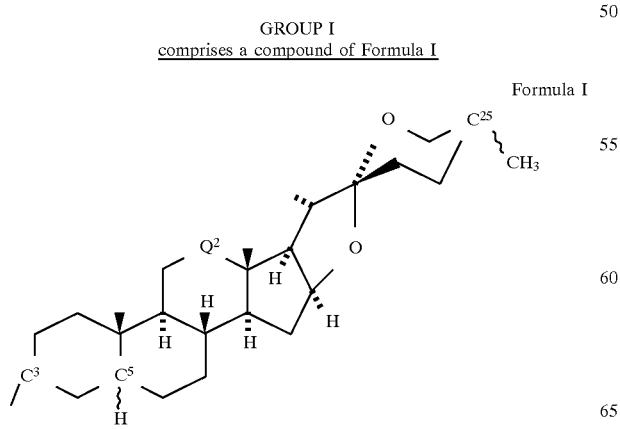

Formula I

-continued
GROUP I
comprises a compound of Formula I

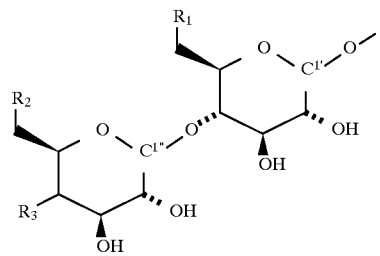

and the pharmaceutically-acceptable salts and hydrates thereof wherein $Q^2$ is carbonyl, methylene,

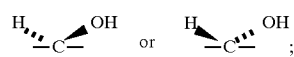

$R_1$, $R_2$, and $R_3$ and each independently hydrogen, hydroxy, halo, amino, azido, $(C_1-C_6)$alkoxy$(C_1-C_6)$alkoxy or —Z—$R_4$;

Z is —NH—C(=O)—, —O—C(=O)—, —O—C(=O)—N($R^5$)—, —NH—C(=O)—N($R^5$)— or —O—C(=S)—N($R^5$)—;

$R_4$ is $(C_1-C_6)$ alkyl, $(C_2-C_{10})$hydroxyalkyl, aryl $(C_1-C_6)$ alkyl, trifluoromethyl$(C_1-C_4)$alkyl, $(C_1-C_4)$ alkyloxycarbonyl$(C_1-C_4)$alkyl or aryl wherein aryl is carbon-linked and is phenyl, furyl, thienyl, pyrrolyl, oxazolyl, isooxazoyl, thiazolyl, isothiazolyl, pyrazolyl, imidazolyl or pyridyl and aryl may be mono- di- or tri-substituted with hydroxy, $(C_1-C_6)$alkyl, $(C_1-C_6)$ alkoxy, halo, nitro or trifluoromethyl; and $R_5$ is hydrogen, $(C_1-C_4)$alkyl or $R_5$ is such that when taken together with the nitrogen to which it is attached and with $R_4$, wherein $R_4$ is a covalent bond, it forms pyrrolidinyl, piperidinyl, piperazinyl or morpholinyl;

with the proviso that $R_1$, $R_2$ and $R_3$ are not all hydroxy; and

GROUP II
comprises a compound of Formula IA

Formula IA

GROUP II
comprises a compound of Formula IA

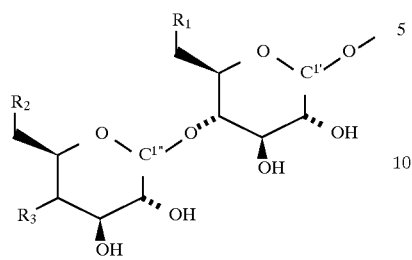

and the pharmaceutically-acceptable salts and hydrates thereof wherein $Q^1$ is carbonyl,

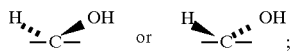

$Q^2$ is methylene, carbonyl,

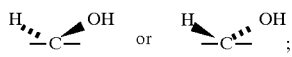

$R_1$, $R_2$, and $R_3$ are each hydrogen, hydroxy, halo, amino, azido, $(C_1-C_6)$alkoxy$(C_1-C_6)$alkoxy or —Z—$R_4$;

Z is —NH—C(=O)—, —O—C(=O)—, —O—C(=O)—N($R_5$)—, —NH—C(=O)—N($R^5$)— or —O—C(=S)—N($R^5$)—;

$R_4$ is $(C_1-C_6)$alkyl, $(C_2-C_{10})$hydroxyalkyl, aryl $(C_1-C_6)$alkyl or aryl wherein aryl is carbon-linked and is phenyl, furyl, thienyl, pyrrolyl or pyridyl and aryl may be mono-, di- or tri-substituted with hydroxy, $(C_1-C_6)$alkyl, $(C_1-C_6)$alkoxy, halo, nitro or trifluoromethyl; and $R_5$ is hydrogen, $(C_1-C_4)$alkyl or $R_5$ is such that when taken together with the nitrogen to which it is attached and with $R_4$, wherein $R_4$ is a covalent bond, it forms pyrrolidinyl, piperidinyl, piperazinyl or morpholinyl;

with the proviso that $R_1$, $R_2$ and $R_3$ are not all hydroxy and b. a therapeutically effective amount of a second compound, said compound an HMG-CoA reductase inhibitor, an HMG-COA synthase inhibitor, an inhibitor of HMG-CoA reductase gene expression, a squalene synthetase inhibitor, a squalene epoxidase inhibitor, a squalene cyclase inhibitor or a lanosterol demethylase inhibitor.

2. The pharmaceutical composition as recited in claim 1 further comprising a pharmaceutical carrier.

3. The pharmaceutical composition according to claim 2 wherein the second compound is a squalene synthetase inhibitor selected from a compound of Formula ZQ

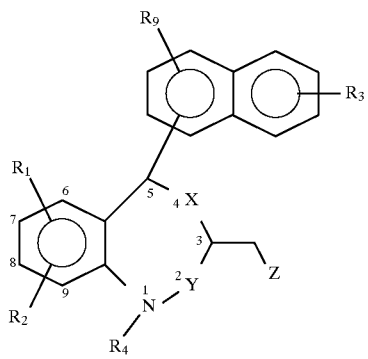

and the pharmaceutically acceptable cationic and anionic salts, prodrugs and stereoisomers thereof wherein X is oxy, thio, —S(O)— or —S(O)$_2$—;

Y is carbonyl or methylene;

$R_1$, $R_2$, $R_3$ and $R_9$ are each independently hydrogen, halo, hydroxyl, trifluoromethyl, $(C_1-C_4)$alkyl, fluorinated $(C_1-C_4)$alkyl having from 1 to 9 fluorines, $(C_1-C_4)$alkoxy, fluorinated $(C_1-C_4)$alkoxy having from 1 to 9 fluorines, $(C_1-C_4)$alkylthio, $(C_1-C_4)$alkylsulfinyl, $(C_1-C_4)$alkylsulfonyl, phenyl, amino, mono-N- or di-N,N-$(C_1-C_4)$alkylamino, carboxyl, $(C_1-C_4)$alkoxycarbonyl, carbamoyl, mono-N- or di-N,N-$(C_1-C_4)$alkylcarbamoyl, $(C_1-C_4)$alkanoylamino, fluorinated $(C_1-C_4)$alkanoylamino having from 1 to 9 fluorines, $(C_1-C_4)$alkylsulfonylamino or fluorinated $(C_1-C_4)$alkylsulfonylamino having from 1 to 9 fluorines, $(C_1-C_6)$alkanoyl, $(C_1-C_6)$alkanoyl$(C_1-C_6)$alkyl, oxazolyl, thiazolyl, isoxazolyl, pyrazolyl or isothiazolyl wherein said preceding heterocycles are carbon linked and wherein $R_1$ and $R_2$ can be taken together to form a five, six or seven membered carbocyclic ring or can be taken together to form methylenedioxyl, ethylenedioxyl or propylenedioxyl and such rings formed by taking $R_1$ and $R_2$ together are fused at the 7 and 8 positions;

$R_4$ is $(C_1-C_7)$alkyl or $(C_3-C_4)$cycloalkylmethyl;

Z is carboxyl, $(C_1-C_4)$alkoxycarbonyl, aminocarbonyl, cyano, hydroxyaminocarbonyl, —C(O)N(H)SO$_2$R$_5$, tetrazol-5yl, 4,5-dihydro-5-oxo-1,2,4oxadiazol-3-yl, tetrazol-5-yl-aminocarbonyl, 3-oxoisoxazolidin-4-yl-aminocarbonyl,

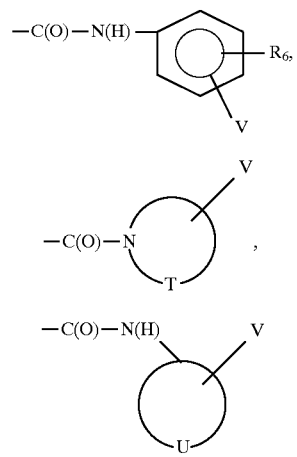

-continued $$-C(O)-N(H)-W-V$$

or $$-C(O)-N(H)-\overset{V}{\underset{(CH_2)_p-R_8}{\diagdown}}$$

$R_5$ is amino or mono-N- or di-N,N-$(C_1-C_4)$alkylamino; $(C_1-C_4)$alkyl optionally substituted with 1 to 9 fluorines, amino, mono-N- or di-N,N-$(C_1-C_4)$alkylamino, carboxyl, $(C_1-C_4)$alkoxycarbonyl, carbamoyl or mono-N- or di-N,N-$(C_1-C_4)$alkylcarbamoyl; phenyl optionally mono- or di-substituted independently with methyl, methoxyl, fluoro, trifluoromethoxyl, carboxyl, $(C_1-C_4)$alkoxycarbonyl, methylthio, methylsulfinyl, methylsulfonyl, $(C_1-C_4)$alkylsulfonylamino or mono-N- or di-N,N-$(C_1-C_4)$alkylaminosulfonyl; or thiazolyl, isothiazolyl, thienyl, furyl, pyridinyl or such heterocycles optionally mono-substituted by carboxyl, or mono- or di-substituted with methyl;

$R_6$ is hydrogen, hydroxyl or methoxyl;

T forms a five to seven membered mono-aza, saturated ring, said ring optionally containing thio and said ring optionally mono-substituted on carbon with hydroxyl;

U forms a three to seven membered saturated carbocyclic ring;

V is $-CO_2R_7$, aminocarbonyl, cyano, tetrazol-5-yl, 4,5-dihydro-5-oxo-1,2,4-oxadiazol-3-yl, tetrazol-5-yl-aminocarbonyl or 3-oxoisoxazolidin-4-yl-aminocarbonyl;

$R_7$ is hydrogen or $(C_1-C_4)$alkyl;

p is 1, 2, 3 or 4;

$R_8$ is hydroxyl, thiol, carboxyl, $(C_1-C_4)$alkoxycarbonyl, carbamoyl, amino, sulfamoyl, $(C_1-C_4)$alkoxy, fluorinated $(C_1-C_4)$alkoxy having from 1 to 9 fluorines, $(C_1-C_4)$alkylthio, $(C_1-C_4)$alkylsulfonyl, $(C_1-C_4)$alkylsulfinyl, mono-N- or di-N,N-$(C_1-C_4)$alkylcarbamoyl, mono-N- or di-N,N-$(C_1-C_4)$alkylamino, $(C_1-C_4)$alkylsulfonylamino, fluorinated $(C_1-C_4)$alkylsulfonylamino having from 1 to 9 fluorines, $(C_1-C_4)$alkanoylamino, fluorinated $(C_1-C_4)$alkanoylamino having from 1 to 9 fluorines, mono-N- or di-N,N-$(C_1-C_4)$alkylaminosulfonyl, ureido, mono-N- or di-N,N-$(C_1-C_4)$ureido, imidazolyl or pyridyl; and W is pyridyl, pyrimidyl, 1,3,4-oxadiazolyl, 1,3,4-thiadiazolyl, thiazolyl, 1,3,4-triazolyl or oxazolyl.

4. The pharmaceutical composition according to 2 claim wherein the second compound is an HMG-CoA reductase inhibitor.

5. The pharmaceutical composition according to claim 4 wherein the first compound is a compound of Group IA wherein $Q^1$ is carbonyl, $$\overset{H_{\prime\prime\prime}}{\underset{-}{\overset{|}{C}}}\overset{OH}{\diagup}$$

or $$\overset{H}{\underset{-}{\overset{|}{C}}}\overset{OH}{\diagup}.$$

6. The pharmaceutical composition according to claim 5 wherein the first compound is (3β, 5α, 25R)-3-[(4",6"-bis[thiazol-2-yl-methylcarbamoyl]-β-D-cellobiosyl)oxy]spirostan-11-one or (3β, 5α, 12β, 25R)-3-[(4",6"-bis[2-(methoxycarbonyl)ethylcarbamoyl]-β-D-cellobiosyl)oxy]-12-hydroxy-spirostan-11-one.

7. The pharmaceutical composition according to claim 6 wherein the second compound is the HMG-CoA reductase inhibitor lovastatin.

8. The pharmaceutical composition according to claim 6 wherein the second compound is the HMG-CoA reductase inhibitor simvastatin.

9. The pharmaceutical composition according to claim 6 wherein the second compound is the HMG-CoA reductase inhibitor pravastatin.

10. The pharmaceutical composition according to claim 6 wherein the second compound is the HMG-CoA reductase inhibitor fluvastatin.

11. The pharmaceutical composition according to claim 6 wherein the second compound is the HMG-CoA reductase inhibitor atorvastatin.

12. The pharmaceutical composition according to claim 6 wherein the second compound is the HMG-CoA reductase inhibitor rivastatin.

13. The pharmaceutical composition according to claim 4 wherein the first compound is (3β,5α,25R)-3-[(4",6"-bis-[2-fluorophenylcarbamoyl]-β-D-cellobiosyl)oxy]spirostan-12-one.

14. The pharmaceutical composition according to claim 13 wherein the second compound is the HMG-CoA reductase inhibitor lovastatin.

15. The pharmaceutical composition according to claim 13 wherein the second compound is the HMG-CoA reductase inhibitor simvastatin.

16. The pharmaceutical composition according to claim 13 wherein the second compound is the HMG-CoA reductase inhibitor pravastatin.

17. The pharmaceutical composition according to claim 13 wherein the second compound is the HMG-CoA reductase inhibitor fluvastatin.

18. The pharmaceutical composition according to claim 13 wherein the second compound is the HMG-CoA reductase inhibitor atorvastatin.

19. The pharmaceutical composition according to claim 13 wherein the second compound is the HMG-CoA reductase inhibitor rivastatin.

20. The pharmaceutical composition according to claim 1 further comprising a pharmaceutical carrier, and wherein the second compound is an HMG-CoA reductase inhibitor and the first compound is a Formula I compound of Group I Formula I

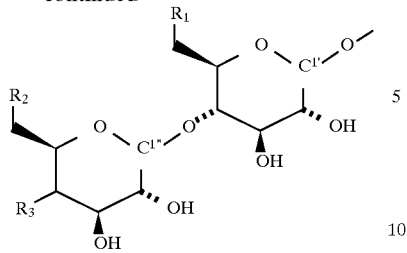

and the pharmaceutically-acceptable salts and hydrates thereof wherein $Q^2$ is carbonyl, methylene,

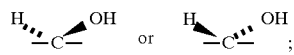

$R_1$, $R_2$, and $R_3$ are each independently hydrogen, hydroxy, halo, amino, azido, $(C_1-C_6)$alkoxy$(C_1-C_6)$alkoxy or —Z—$R_4$;

Z is —NH—C(=O)—, —O—C(=O)—, —O—C(=O)—N($R^5$)—, —NH—C(=O)—N($R^5$)— or —O—C(=S)—N($R^5$)—;

$R_4$ is $(C_1-C_6)$alkyl, $(C_2-C_{10})$hydroxyalkyl, aryl $(C_1-C_6)$alkyl, trifluoromethyl$(C_1-C_4)$alkyl, $(C_1-C_4)$alkyloxycarbonyl$(C_1-C_4)$alkyl or aryl wherein aryl is carbon-linked and is phenyl, furyl, thienyl, pyrrolyl, oxazolyl, isooxazoyl, thiazolyl, isothiazolyl, pyrazolyl, imidazolyl or pyridyl and aryl may be mono- di- or tri-substituted with hydroxy, $(C_1-C_6)$alkyl, $(C_1-C_6)$alkoxy, halo, nitro or trifluoromethyl; and $R_5$ is hydrogen, $(C_1-C_4)$alkyl or $R_5$ is such that when taken together with the nitrogen to which it is attached and with $R_4$, wherein $R_4$ is a covalent bond, it forms pyrrolidinyl, piperidinyl, piperazinyl or morpholinyl; with the proviso that $R_1$, $R_2$ and $R_3$ are not all hydroxy.

21. The pharmaceutical composition according to claim 1 further comprising a pharmaceutical carrier, and wherein the second compound is an HMG-CoA reductase inhibitor and the first compound is a Formula IA compound of Group II Formula IA

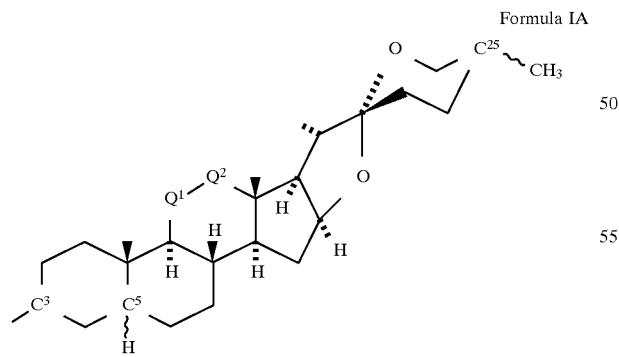

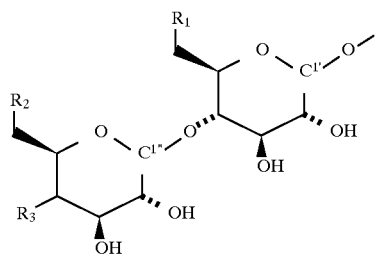

and the pharmaceutically-acceptable salts and hydrates thereof wherein $Q^1$ is carbonyl,

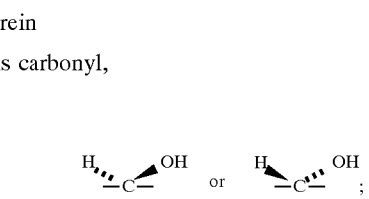

$Q^2$ is methylene, carbonyl,

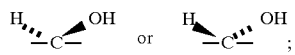

$R_1$, $R_2$, and $R_3$ are each independently hydrogen, hydroxy, halo, amino, azido, $(C_1-C_6)$alkoxy$(C_1-C_6)$alkoxy or —Z—$R_4$;

Z is —NH—C(=O)—, —O—C(=O)—, —O—C(=O)—N($R_5$)—, —NH—C(=O)—N($R^5$)— or —O—C(=S)—N($R^5$)—;

$R_4$ is $(C_1-C_6)$alkyl, $(C_2-C_1)$hydroxyalkyl, aryl $(C_1-C_6)$alkyl or aryl wherein aryl is carbon-linked and is phenyl, furyl, thienyl, pyrrolyl or pyridyl and aryl may be mono-, di- or tri-substituted with hydroxy, $(C_1-C_6)$alkyl, $(C_1-C_6)$alkoy, halo, nitro or trifluoromethyl; and $R_5$ is hydrogen, $(C_1-C_4)$alkyl or $R_5$ is such that when taken together with the nitrogen to which it is attached and with $R_4$, wherein $R_4$ is a covalent bond, it forms pyrrolidin, piperidinyl, piperazinyl or morpholinyl;

with he proviso that $R_1$, $R_2$ and $R_3$ are not all hydroxy.

* * * * *